US012186348B2

(12) United States Patent
Liu et al.

(10) Patent No.: US 12,186,348 B2
(45) Date of Patent: Jan. 7, 2025

(54) **GLYCAN STRANDS AND OLIGOSACCHARIDES DERIVED FROM *STREPTOCOCCUS* BACTERIA**

(71) Applicant: Meharry Medical College, Nashville, TN (US)

(72) Inventors: Bindong Liu, Brentwood, TN (US); Qiujia Shao, Brentwood, TN (US)

(73) Assignee: Meharry Medical College, Nashville, TN (US)

( * ) Notice: Subject to any disclaimer, the term of this patent is extended or adjusted under 35 U.S.C. 154(b) by 1015 days.

(21) Appl. No.: 17/057,599

(22) PCT Filed: May 23, 2019

(86) PCT No.: PCT/US2019/033796
§ 371 (c)(1),
(2) Date: Nov. 20, 2020

(87) PCT Pub. No.: WO2019/226920
PCT Pub. Date: Nov. 28, 2019

(65) Prior Publication Data
US 2021/0187042 A1    Jun. 24, 2021

Related U.S. Application Data

(60) Provisional application No. 62/675,483, filed on May 23, 2018.

(51) Int. Cl.
| | | |
|---|---|---|
| *A61K 35/74* | (2015.01) |
| *A61K 9/00* | (2006.01) |
| *A61K 31/34* | (2006.01) |
| *A61K 31/427* | (2006.01) |
| *A61K 31/439* | (2006.01) |
| *A61K 31/4418* | (2006.01) |
| *A61K 31/513* | (2006.01) |
| *A61K 31/52* | (2006.01) |
| *A61K 31/537* | (2006.01) |
| *A61K 31/5377* | (2006.01) |
| *A61K 31/675* | (2006.01) |
| *A61K 31/702* | (2006.01) |
| *A61K 31/7072* | (2006.01) |
| *A61K 31/715* | (2006.01) |
| *A61K 38/16* | (2006.01) |
| *A61K 38/21* | (2006.01) |
| *A61K 45/06* | (2006.01) |
| *A61K 47/60* | (2017.01) |
| *A61P 31/18* | (2006.01) |
| *C07H 3/06* | (2006.01) |
| *C08B 37/00* | (2006.01) |

(52) U.S. Cl.
CPC ........... *A61K 35/74* (2013.01); *A61K 9/0014* (2013.01); *A61K 9/0019* (2013.01); *A61K 31/34* (2013.01); *A61K 31/427* (2013.01); *A61K 31/439* (2013.01); *A61K 31/4418* (2013.01); *A61K 31/513* (2013.01); *A61K 31/52* (2013.01); *A61K 31/5377* (2013.01); *A61K 31/675* (2013.01); *A61K 31/702* (2013.01); *A61K 31/7072* (2013.01); *A61K 31/715* (2013.01); *A61K 38/162* (2013.01); *A61K 38/212* (2013.01); *A61K 45/06* (2013.01); *A61K 47/60* (2017.08); *A61P 31/18* (2018.01); *C07H 3/06* (2013.01); *C08B 37/0003* (2013.01)

(58) Field of Classification Search
None
See application file for complete search history.

(56) References Cited

U.S. PATENT DOCUMENTS 10,751,402 B2    8/2020    Anderson et al.

FOREIGN PATENT DOCUMENTS

| RU | 2441906 C2 * | 2/2012 |
| RU | 2563354 | 9/2015 |
| WO | 2013181348 | 12/2013 |

OTHER PUBLICATIONS

Vollmer et al. The Cell Wall of *Streptococcus pneumoniae*. Microbiol Spectrum 7(3):GPP3-0018-2018. doi:10.1128/microbiolspec.GPP3-0018-2018.*
Kampff et al. vol. 69, 2023, 108279, ISSN 0734-9750, https://doi.org/10.1016/j.biotechadv.2023.108279.*
The Written Opinion of the International Searching Authority of PCT/US2019/033796, Jul. 18, 2019.
Wang, Z. et al., Heat-Stable Molecule Derived from *Streptococcus cristatus* Induces APOBEC3 Expression and Inhibits HIV-1 Replication, PLoS One, 2014, vol. 9, No. 8, e106078.
Bui. N. et al., Isolation and analysis of cell wall components from *Streptococcus pneumoniae*, Analytical Biochemistry, 2011, vol. 421, pp. 657-666.
International Preliminary Report on Patentability of PCT/US2019/033796, Nov. 24, 2020.
Girardin, Stephen E. et al., Nod2 Is a General Sensor of Peptidoglycan through Muramyl Dipeptide (MDP) Detection, The Journal of Biological Chemistry, vol. 278, No. 11, pp. 8869-8872, 2003.
Travassos, Leonardo H., et al., Toll-like recpetor 2-dependent bacterial sensing does not occur via peptidoglycan recognition, European Molecular Biology Organization, vol. 5, No. 10, pp. 1000-1006, 2004.

* cited by examiner

*Primary Examiner* — Oluwatosin A Ogunbiyi
(74) *Attorney, Agent, or Firm* — Bradley Arant Boult Cummings LLP; Phil Walker; Jessica L. Zurlo

(57) ABSTRACT

Compositions of glycan strands and oligosaccharides derived from gram-positive bacteria and methods of use thereof are provided. The disclosed compositions have inhibitory activity toward both early and late stages of viral infection and transmission. The disclosed compositions may be used to treat and/or prevent infection and transmission of viruses, such as HIV, to upregulate one or both of AG3 and MX2, to enhance immune function, and/or to inhibit replication of a virus.

16 Claims, 19 Drawing Sheets

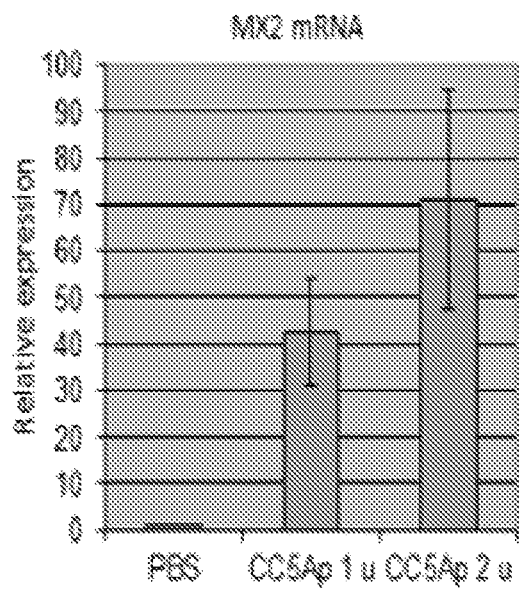
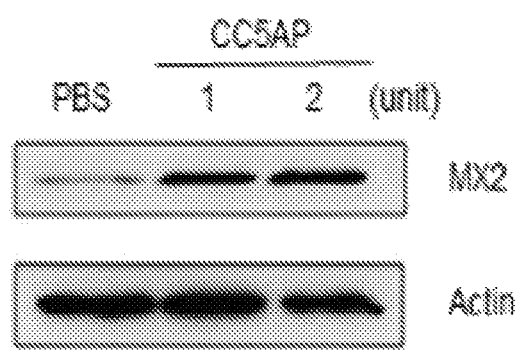
FIG. 6A  FIG. 6B
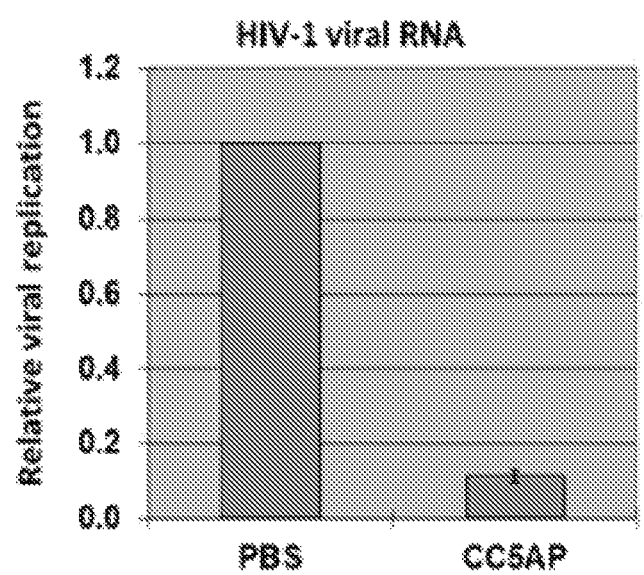
FIG. 6C

GLYCAN STRANDS AND OLIGOSACCHARIDES DERIVED FROM *STREPTOCOCCUS* BACTERIA

STATEMENT REGARDING FEDERALLY SPONSORED RESEARCH

This invention was made with government support under grant number 2SC1GM089269 awarded by the National Institutes of Health. The government has certain rights in the invention.

In this context, "government" refers to the government of the United States of America.

FIELD OF THE DISCLOSURE

The present disclosure relates generally to molecules derived from gram-positive bacteria, and their use in methods of treatment and/or prevention of diseases and medical conditions, for example, human immunodeficiency virus (HIV).

BACKGROUND

Human immunodeficiency virus, known as HIV, is a virus that attacks the body's immune system, specifically the CD4 cells, often called T cells. There were approximately 36.7 million people worldwide living with HIV/AIDS at the end of 2016. The number of people living with HIV continues to increase worldwide. Without an effective vaccine, treatment of infection and prevention of transmission remain the only options for patients. Although there are clinically approved drugs for treatment of HIV infection as well as drug combinations that can effectively manage replication, eradication of the virus remains out of reach. A patient infected with HIV must undergo lifelong treatment and cessation of treatment almost universally results in rebound of viremia. Additionally, the effectiveness of treatment is limited by patients' incomplete adherence to treatment schedules (often owing to drug side effects and patient complacency) and by viral resistance to therapy.

The pathogenic mechanisms underlying HIV infection and disease are extremely complex and make it difficult to develop treatments. While there have been advancements, there still remains a need to develop more effective treatments for viruses, such as HIV, that boost the host innate immune system and take advantage of the antiviral function of host cellular factors.

SUMMARY

The problems described above, as well as others, are addressed by the following inventions, although it is to be understood that not every embodiment of the inventions described herein will address each of the problems described above, it has been unexpectedly discovered that glycan strand and oligosaccharide molecules derived from gram-positive bacteria treat and prevent infection and transmission of viruses such as HIV.

In a first aspect, a method of making a glycan strand extract from a *Streptococcus* cell is provided, the method including isolating a cell wall component from the *Streptococcus* cell to form an isolated cell wall composition; cleaving the bonds between glycan and at least one of teichoic acid and peptides in the isolated cell wall composition to form a first digest; and reducing the concentration of the at least one of teichoic acid and peptides in the first digest to form the glycan strand extract.

In a second aspect, a composition is provided including a soluble glycan strand derived from gram-positive bacteria, wherein the soluble glycan strand includes from two to 100 monosaccharide units.

In a third aspect, a composition is provided including an oligosaccharide derived from a *Streptococcus* cell, wherein the oligosaccharide includes from two to 100 monosaccharide units.

In a fourth aspect, a pharmaceutical composition is provided including a pharmaceutically acceptable carrier and an effective amount of an oligosaccharide derived from a *Streptococcus* cell, wherein the oligosaccharide includes from two to 100 monosaccharide units.

In a fifth aspect, a method of treating or preventing one or both of human immunodeficiency virus (HIV) and hepatitis B virus (HBV) in a subject is provided, the method including administering to the subject an effective amount of the pharmaceutical composition provided above to a subject in need of treatment thereof.

In a sixth aspect, a method of upregulating one or both of apolipoprotein B mRNA-editing enzyme, catalytic polypeptide-like 3G (A3G) and myxovirus resistance 2 (MX2) in a subject is provided, the method including administering to the subject an effective amount of the pharmaceutical composition provided above to enhance expression of one or both of A3G and MX2.

In a seventh aspect, a method of enhancing immune function in a subject is provided, the method including administering to the subject an effective amount of the pharmaceutical composition provided above to enhance immune function.

In an eighth aspect, a method of inhibiting replication of one or more viruses in a cell is provided, the method including contacting the cell with the composition provided above to inhibit viral replication.

In a ninth aspect, a method of inhibiting viral infection of a cell is provided, the method including contacting the cell with an effective amount of the composition provided above to inhibit viral entry into the cell.

BRIEF DESCRIPTION OF THE DRAWINGS

Further features and advantages of the invention can be ascertained from the following detailed description that is provided in connection with the drawings described below:

FIG. 6A is a bar graph showing that oligosaccharide molecules derived from *Streptococcus cristatus* increase expression of MX2 mRNA in THP-1 cells.

FIG. 6B is a Western-blot analysis showing that oligosaccharide molecules derived from *Streptococcus cristatus* increase expression of MX2 protein in THP-1 cells.

FIG. 6C is a bar graph showing that viral release from cells treated with oligosaccharide molecules derived from *Streptococcus cristatus* was significantly lower than that observed in the controls. Shown are averages±standard deviation of triplicate samples.

DETAILED DESCRIPTION

I. Definitions

Figure 1:
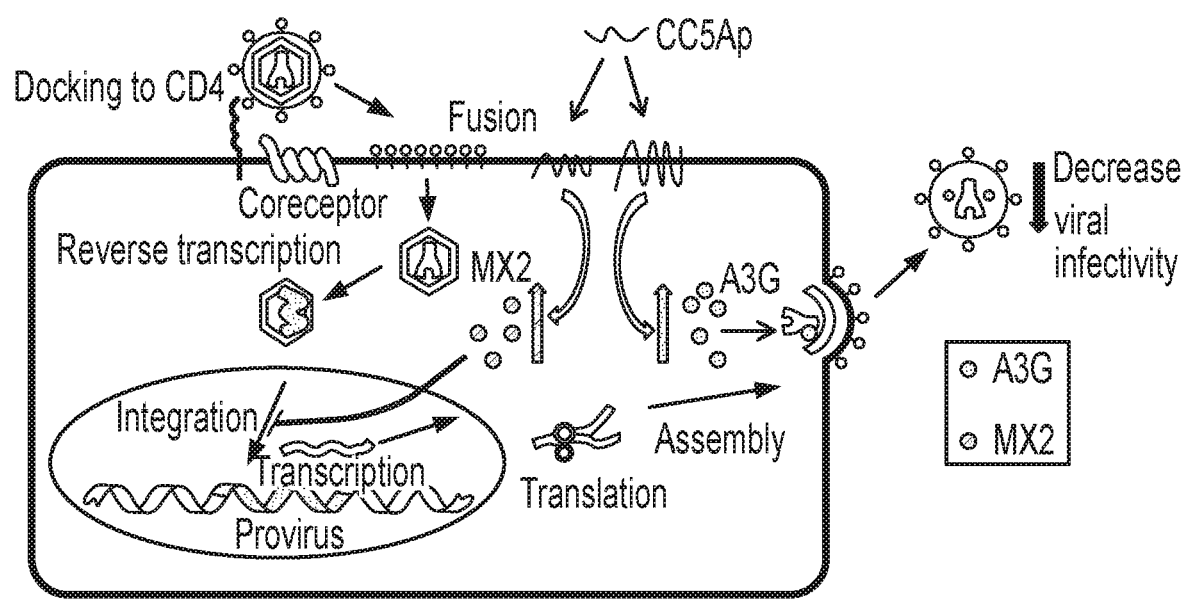
FIG. 1 is a schematic diagram showing at least one mechanism by which the disclosed molecules synergistically target the early and late stages of HIV-1 replication.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

As used herein, the singular forms "a," "an," and "the" include plural referents unless the context clearly dictates otherwise.

Recitation of ranges of values herein are merely intended to serve as a shorthand method of referring individually to each separate value falling within the range, unless otherwise indicated herein, and each separate value is incorporated into the specification as if it were individually recited herein.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5% of a given value or range of values, and still more preferably within 1% of a given value or range of values. Numerical quantities given in this description are approximate unless stated otherwise, meaning that the term "about" or "approximately" can be inferred when not expressly stated. Numerical quantities given in the claims are exact unless stated otherwise.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Terms such as "at least one of A and B" should be understood to mean "only A, only B, or both A and B." The same construction should be applied to longer list (e.g., "at least one of A, B, and C"). The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

The terms "treatment", "treat" and "treating" as used herein refers a course of action (such as implanting a medical device) initiated after the onset of a clinical manifestation of a disease state or condition so as to eliminate, or reduce such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is or will be as the result of a condition that is treatable by a method or device of the present disclosure.

The terms "prevention", "prevent", "preventing", "suppression", "suppress" and "suppressing" as used herein refer to a course of action (such as implanting a medical device) initiated prior to the onset of a clinical manifestation of a disease state or condition so as to prevent or reduce such clinical manifestation of the disease state or condition. Such preventing and suppressing need not be absolute to be useful. The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or device of the disclosure.

In this disclosure terms such as "administering" or "administration" include acts such as prescribing, dispensing, giving, or taking a substance such that what is prescribed, dispensed, given, or taken is actually contacts the patient's body externally or internally (or both). It is specifically contemplated that instructions or a prescription by a medical professional to a subject or patient to take or otherwise self-administer a substance is an act of administration.

The terms "increase," "enhance," "stimulate," and "induce" (and like terms) generally refer to the act of improving or increasing, either directly or indirectly, a function or behavior relative to the natural, expected, or average or relative to current conditions.

The term "pharmaceutically acceptable carrier" refers to one or more compatible solid or liquid fillers, diluents, or encapsulating substances that does not cause significant irritation to a human or other vertebrate animal and does not abrogate the biological activity and properties of the administered compound.

The terms "individual," "subject," and "patient" are used interchangeably herein, and refer to a mammal, including, but not limited to, humans, rodents, such as mice and rats, and other laboratory animals.

The terms "therapeutically effective amount" and "effective amount" refer to a dosage sufficient to treat, inhibit, prevent, reduce the severity of, or alleviate one or more symptoms of the disease being treated or to otherwise provide a desired pharmacologic and/or physiologic effect.

II. Molecules Derived from Gram-Positive Bacteria

The present disclosure provides molecules derived from gram-positive bacteria that have inhibitory activity toward at least one of early and late stages of viral infection and transmission. In one embodiment, the disclosed molecules enhance one or both of A3G and MX2 expression, which results in multiple layers of defense against viral, e.g., HIV, replication and transmission. MX2 inhibits viral integration (the early stage of HIV-1 replication) and AG3 reduces viral infectivity upon infection of new target cells (which is the late stage of viral replication). Without being bound by any particular theory, it is believed that the incoming virus will be targeted by over-expressed MX2 through reduction of its viral cDNA integration, and for the escaped viruses, the over-expressed AG3 will be encapsulated into the released virions to carry out the antiviral effects on the next round of viral infection. FIG. 1 shows a schematic of the disclosed molecules synergistically targeting the early and late stages of HIV-1 replication. Accordingly, by enhancing one or both of A3G and MX2 expression, the disclosed molecules can block at least one of early and late stages of viral replication and transmission and provide fewer chances for viruses, such as HIV, to generate resistance to the disclosed molecules.

The disclosed molecule may include any molecule derived from an active fraction of gram-positive bacteria that targets a stage of at least one viral replication path, for example, a HIV replication path. The term "active fraction" as used herein refers to an extract of the bacteria that exhibits biological activity. In one embodiment, the disclosed molecule is a soluble glycan strand derived from gram-positive bacteria that targets a stage of at least one viral replication path. In another embodiment, the disclosed molecule includes an oligosaccharide derived from gram-positive bacteria that targets a stage of at least one viral replication path. In still another embodiment, the disclosed molecule may include a plurality of any of the molecules disclosed above. For example, the disclosed molecule may include two or more soluble glycan strands, two or more oligosaccharides, or combinations thereof.

The molecules disclosed herein may be derived from any gram-positive bacteria. In one embodiment, the disclosed molecules may be derived from oral commensal bacteria that is gram-positive. Without being bound by any particular theory, it is believed that oral commensal bacteria may prevent HIV transmission by boosting oral innate immunity. For example, the disclosed molecules may be derived from *Streptococcus, Actinomyces, Lactobacterium, Peptostreptococcus, Staphylococcus*, and *Propionibacterium* cells. In some embodiments, the disclosed molecules are derived from a *Streptococcus* cell. For instance, the disclosed molecules may be derived from *Streptococcus cristatus* or *Streptococcus mutans*. In one embodiment, the disclosed molecule is a glycan strand or oligosaccharide derived from *Streptococcus cristatus*. In another embodiment, the disclosed molecules may include one or more glycan strands derived from *Streptococcus cristatus* or *Streptococcus mutans*, one or more oligosaccharides derived from *Streptococcus cristatus* or *Streptococcus mutans*, or combinations thereof.

In certain embodiments, the disclosed molecules are water-soluble and heat stable. For example, the disclosed molecules may be active after boiling in 5% SDS for about 30 minutes. In another embodiment, the disclosed molecules have a molecular weight of more than about 450 Da. Some embodiments of the molecule have a molecular weight of at least 460, 470, 480, 490, and 495 Da. In further embodiments the disclosed molecules may have a molecular weight of more than about 750 Da. In still another embodiment, the disclosed molecules are non-cytotoxic. For example, the disclosed molecules are not toxic to mammalian cells. In yet another embodiment, the disclosed molecules are non-immunogenic. Without being bound by any particular theory, it is believed that the disclosed molecules are non-inflammatory and do not enhance inflammatory cytokine production.

The disclosed molecules are composed of monosaccharide units. The disclosed molecules may include two or more monosaccharide units. In one embodiment, the disclosed molecules include from two to 100 monosaccharide units. In another embodiment, the disclosed molecules include from two to 50 monosaccharide units. In still another embodiment, the disclosed molecules include from two to 25 monosaccharide units. In yet another embodiment, the disclosed molecules include from five to twenty monosaccharide units. For example, the disclosed molecules may include from two to ten monosaccharide units.

In one embodiment, the structure of the disclosed molecules includes at least one N-acetylglucosamine (GlcNAc)

monosaccharide unit and at least one N-acetylmuramic acid (MurNAc) monosaccharide unit. In another embodiment, the structure may include a plurality of GlcNAc and MurNAc monosaccharide units. In this embodiment, the disclosed molecules may include a plurality of alternating GlcNAc and MurNAc monosaccharide units.

In certain embodiments, the disclosed molecule is a grouping of two or more oligosaccharides derived from gram-positive bacteria, such as *Streptococcus cristatus* or *Streptococcus mutans*. In this embodiment, each oligosaccharide may have differing numbers of monosaccharide units. For instance, the disclosed molecule may include a grouping of at least three oligosaccharide molecules having the following structures: GlcNAc-MurNAc, MurNAc-GlcNAc-MurNAc, and GlcNAc-MurNAc-GlcNAc-MurNAc. In another embodiment, the disclosed molecule may include a grouping of at least five oligosaccharide molecules. In still another embodiment, the disclosed molecule may include a grouping of at least eight oligosaccharide molecules. The disclosed oligosaccharides may have a mass/charge (m/z) ratio ranging from about 400 to about 2000. In another embodiment, the disclosed oligosaccharides have a mass/charge (m/z) ratio ranging from about 450 to 1000.

The molecules disclosed herein can be made by any method known in the art. Examples of such methods are described in a variety of articles, such as Bui N K et al. 2012. "isolation and analysis of cell wall components from *Streptococcus pneumoniae*." *Analytical Biochemistry* 421: 657-666. The molecules disclosed herein may also be synthesized chemically.

In one embodiment, a glycan strand extract and/or a glycan strand may be made by isolating a cell wall component from a cell of gram-positive bacteria, for example, a *Streptococcus* cell, to form an isolated cell wall composition. The bonds between the glycan and the wall teichoic acid and/or peptides of the cell wall composition are then cleaved to form a digest. In this embodiment, the method further includes cleaving the bonds in the peptidoglycan between the glycan and the teichoic acid; cleaving the bonds in the peptidoglycan between the glycan and the peptides; and/or cleaving a glycosidic bond in the glycan group. The bonds may be cleaved using any reagent capable of splitting the chemical bonds between the glycan and the wall teichoic acid and/or peptides. For example, the reagent may include hydrofluoric acid, LytA, amidase, or combinations thereof. In order to form a glycan strand extract and/or a glycan strand, substantially a non-saccharide compounds are removed from the digest. For instance, the concentration(s) of the wall teichoic acid and/or peptides is reduced to form the glycan strand extract and/or the glycan strand derived from the gram-positive bacteria, for example, a *Streptococcus* cell.

In another embodiment, the glycan strand extract may undergo further treatment to form a second digest including an oligosaccharide molecule. For example, the glycan strand extract may be treated with mutanolysin to form a second digest that includes an oligosaccharide derived from the gram-positive bacteria, for example, a *Streptococcus* cell.

III. Pharmaceutical Compositions

In one embodiment, the active molecules are in the form of compositions, such as but not limited to, pharmaceutical compositions. Pharmaceutical compositions are provided including one or more of the disclosed active molecules, and optionally pharmaceutically acceptable diluents, preservatives, solubilizers, emulsifiers, adjuvants, excipients, and/or carriers.

To form a pharmaceutically acceptable composition suitable for administration, such compositions will contain a therapeutically effective amount of an active molecule. The disclosed compositions are administered to a subject in an amount sufficient to deliver a therapeutically effective amount of the active molecule so as to be effective in the treatment and prevention methods disclosed herein. The precise dosage may vary according to a variety of factors such as, but not limited to, the subject's condition, weight, sex, and age.

In this aspect, the selected dosage depends upon the desired therapeutic effect, on the route of administration, and on the duration of the treatment desired. Generally, for intravenous injection or infusion, the dosage may be lower.

Alternatively, the pharmaceutical compositions may be formulated to achieve a desired concentration of the active molecule at a target tissue of the subject. For example, the disclosed pharmaceutical compositions may be formulated to achieve desired concentrations at one or more tissues susceptible to infection including, but not limited to, cervical tissue, blood, oral mucosa, or rectal tissue. In one embodiment, the composition includes an effective amount of active molecule sufficient to achieve a concentration of 50 µg/mL to 300 µg/mL of the active molecule at one or more tissues susceptible to infection, for example, cervical tissue, blood, oral mucosa, or rectal tissue. In another embodiment, the composition includes an effective amount of active molecule sufficient to achieve a concentration of 100 µg/mL to 300 µg/mL of the active molecule at one or more tissues susceptible to infection, for example, cervical tissue, blood, oral mucosa, or rectal tissue.

The pharmaceutical compositions may be formulated to be provided to the subject in any method known in the art. For instance, the pharmaceutical compositions may be formulated for administration by parenteral (for example, intramuscular, intraperitoneal, intravitreally, intravenous (IV), or subcutaneous injection), enteral, transmucosal (for example, nasal, vaginal, rectal, or sublingual), or transdermal routes of administration and can be formulated in dosage forms appropriate for each route of administration. The disclosed compositions may be formulated to be administered only once to the subject or more than once to the subject. Furthermore, when the compositions are administered to the subject more than once, a variety of regimens may be used, such as, but not limited to, once per day, once per week, once per month or once per year. The compositions may also be formulated to be administered to the subject more than one time per day. The therapeutically effective amount of the active molecule and appropriate dosing regimens may be identified by routine testing in order to obtain optimal activity, while minimizing any potential side effects. In addition, formulation for co-administration or sequential administration of other agents may be desirable.

In certain embodiments, the disclosed compositions may be formulated to be administered systemically, such as by intravenous administration, or locally such as by subcutaneous injection. Typically, local administration causes an increased localized concentration of the composition which is greater than that which can be achieved by systemic administration.

The disclosed compositions may further include agents which improve the solubility, half-life, absorption, etc. of the active molecule. Furthermore, the disclosed compositions may further include agents that attenuate undesirable side effects and/or decrease the toxicity of the active molecule. Examples of such agents are described in a variety of texts, such as, but not limited to, Remington: The Science and Practice of Pharmacy (20th Ed., Lippincott, Williams & Wilkins, Daniel Limmer, editor).

1. Formulations for Parenteral Administration

The disclosed compositions may be formulated for parenteral administration, for example, intramuscular, intraperitoneal, intravenous, or subcutaneous administration. In some embodiments, the compositions disclosed herein are formulated for parenteral injection, for example, in an aqueous solution. The formulation may also be in the form of a suspension or emulsion. The disclosed compositions may optionally include one or more of the following for parenteral administration: diluents, sterile water, buffered saline of various buffer content (for example, Tris-HCl, acetate, phosphate), pH and ionic strength, ionic liquids, and HPßCD; and additives such as detergents and solubilizing agents (for example, TWEEN® 20 (polysorbate-20), TWEEN® 80 (polysorbate-80)), anti-oxidants (for example, ascorbic acid, sodium metabisulfite), and preservatives (for example, Thimersol, benzyl alcohol) and bulking substances (for example, lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

In some embodiments, the disclosed compositions are formulated for enteral administration including oral, sublingual, and rectal delivery. In one embodiment, the disclosed compositions are administered in solid dosage form. Suitable solid dosage forms include tablets, capsules, pills, lozenges, cachets, pellets, powders, granules, or incorporation of the material into particulate preparations of polymeric compounds such as polylactic acid, polyglycolic acid, or into liposomes. In another embodiment, the disclosed compositions are administered in liquid dosage form. Examples of liquid dosage forms for enteral administration include pharmaceutically acceptable emulsions, solutions, suspensions, and syrups, which may contain other components including inert diluents; preservatives; binders; stabilizers; adjuvants such as wetting agents, emulsifying and suspending agents; and sweetening, flavoring, and perfuming agents.

Controlled release oral formulations, for example, delayed release or extended release formulations, may also be desirable. For example, the disclosed compounds may be encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings (for example, delayed release or extended release coatings) prior to incorporation into the finished dosage form. In still another embodiment, the disclosed compounds may be dispersed in a matrix material, which gels or emulsifies upon contact with an aqueous medium. Such matrices may be formulated as tablets or as fill materials for hard and soft capsules.

For enteral formulations, the location of release may be the stomach, the small intestine (the duodenum, the jejunem, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance, a coating impermeable to at least pH 5.0 is essential. Examples of common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

In other embodiments, the disclosed compositions are formulated for topical application. Topical dosage forms, such as, but not limited to, lotions, sprays, ointments, creams, pastes, and emulsions, containing the active molecule, can be admixed with penetration enhancers and a variety of carrier materials well known in the art, such as alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery, or may be applied to a bandage or dressing for delivery directly to the site of a wound or cutaneous injury.

4. Formulations for Transmucosal Administration

In some embodiments, the disclosed compositions may be formulated for transmucosal administration. Transmucosal administration refers to a route of administration in which the drug is diffused through the mucous membrane. For instance, the disclosed compositions may be formulated for inhalation, nasal, oral (sublingual, buccal), vaginal, rectal, or ocular routes. Formulations for administration to the mucosa will typically be spray dried drug particles, which may be incorporated into, for example, a tablet, gel, capsule, suspension, emulsion, cream, foam, ointment, tampon, enema solution, or suppository.

5. Dentifrices

The pharmaceutical composition may be a dentifrice. The dentifrice may be selected from the group consisting of a paste, a get, a mouthwash, a powder, and a tooth soap. In some embodiments of the composition, the dentifrice is a paste or gel comprising at least one of an abrasive, a surfactant, a humectant, and a thickener. Such abrasives include, but are not limited to, hydrated silica, dicalcium phosphate dihydrate, calcium carbonate, sodium bicarbonate, calcium pyrophosphate, and alumina. Such surfactants include, but are not limited to, sodium lauryl sulfate, sodium N-lauryl sarcosinate, pluronics, sodium lauryl sulfoacetate. Such anticaries agents include, but are not limited to, fluoride. Such tartar control ingredients include, but are not limited to, tetrasodium pyrophosphate, Gantrez S-70, sodium tripolyphosphate, and methyl vinyl ether/maleic anhydride copolymer. The dentifrice may further comprise one or more of: water; pH buffers; humectants (to prevent dry-out and increase pleasant mouth feel) such as, but not limited to glycerin, sorbitol, polypropylene glycol, xylitol, and polyethylene glycol; thickeners such as but not limited to silica thickeners, sodium aluminum silicates, and days; gums such as but not limited to sodium carboxymethyl cellulose, cellulose ethers, xantham gum, carrageenans, sodium alginate, and carbopols; antibacterial agents; flavoring agents such as, but not limited to water-insoluble essential oils; sweetening agents such as, but not limited to saccharin, dextrose, levulose, cyclamate, aspartate; coloring agents; and binders to provide consistency and shape.

For oral administration by mouthwash, the active molecule may be combined with one or more of: water and alcohol (such as ethyl alcohol). The mouthwash may further comprise one or more of: surfactants, tartar control ingredients, anticaries agents, buffers, humectants, antibacterial agents, flavoring agents, and coloring agents as described in the preceding section In a specific embodiment, the dentifrice is a powder comprising any of the abrasives described above. The powder may further comprise any of the dry components provided above as suitable in a toothpaste. In another specific embodiment, the dentifrice is a tooth soap comprising one or more of oil and water. The oil may be any that is known to be suitable in a tooth soap, such as, but not limited to olive oil, coconut oil, an essential oil, and peppermint oil.

IV. Vaccines

In one embodiment, the disclosed molecules are in the form of a vaccine for immunizing a subject against infection of a virus, including but not limited to any of the viruses described above. The vaccine may contain one or more antigens in addition to the molecules disclosed above, in a specific example, the disclosed molecules may be in the form of a vaccine for immunizing a subject against infection of HIV. In one embodiment, the vaccine includes one or more of the disclosed molecules combined with one or more pharmaceutically acceptable stabilizers, carriers, preservatives cell culture materials, inactivating agents, antibiotics and/or adjuvants. Pharmaceutically acceptable carriers suitable for use include, but are not limited to, any of those described above; some embodiments of the vaccine include as the carrier one or more of saline, phosphate-buffered saline, Minimal essential media (MEM), or MEM with HEPES buffer. Stabilizers include, but are not limited to, sucrose, gelatin, peptone, digested protein extracts (such as NZ-Amine or NZ-Amine AS), sorbitol, lactose, mannitol, glycerol, Medium 199, urea, and monosodium glutamate. Adjuvants include any compositions comprised of one or more substances that enhances the immunogenicity and efficacy of the disclosed molecules when combined with the disclosed molecules in a vaccine composition. Examples of such adjuvants include aluminum gels, aluminum salts, squalene, squalene emulsion, and monophosphoryl lipid A. Preservatives may be added to increase the shelf life of the vaccine or prevent microbiological contamination. Examples of commonly used preservatives include ethylmercury, antibiotics (e.g., neomycin, streptomycin, polymyxin b, gentamicin and kanamycin), gelatin, and monosodium glutamate. Inactivating agents may be present to ensure that any killed or attenuated infectious agents are inactivated. Such inactivating agents include without limitation formaldehyde and glutaraldehyde. The vaccine may be prepared by any method known in the art.

V. Methods of Treatment and Prevention

The disclosed compositions can be used, for example, to treat and/or prevent infection and transmission of viruses, such as HIV, to upregulate one or both of AG3 and MX2, to enhance immune function, and to inhibit replication of a virus.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art.

The disclosed active molecules have been found to upregulate A3G and/or MX2 expression and inhibit viral replication, for example, HIV replication. A3G and MX2 are potent host restriction factors of HIV replication that target different stages of HIV replication. Without being bound by any particular theory, it is believed that A3G targets a late stage of HIV replication by incorporating into viral particles and causing HIV to be non-infections, while MX2 targets early stage HIV replication by inhibiting viral integration and rendering cells resistant to HIV infection. Without being bound by any particular theory, it is also believed that the disclosed molecules and compositions have multi-inhibitory effects against viral replication and enhance innate immunity by upregulating A3G and/or MX2 expression. More specifically, it is believed that the disclosed molecules and compositions interact with a TLR mediated pathway and/or stimulate the innate immune system, which in turn suppresses HIV replication by actively increasing proteins that block both early and late HIV replication.

In one embodiment, the present disclosure provides for a method of treatment and/or prevention of infection and/or transmission of a virus in a subject in need thereof, the method including administering any of the disclosed active molecules or pharmaceutical compositions to the subject in a therapeutically effective amount. Such active molecules may be, for example, a glycan strand or an oligosaccharide derived from *Streptococcus cristatus* or *Streptococcus mutans*. Viruses that can be prevented or treated by the disclosed compositions include, but are not limited to, human immunodeficiency virus (HIV), such as human immunodeficiency virus type I (HIV-I) and human immunodeficiency virus type II (HIV-II), hepatitis B virus (HBV), human T-cell leukemia virus type 1 (HTLV-1), human papillomavirus (HPV), herpes simplex virus (HSV), and hepatitis C virus (HCV). The method may also be useful for treatment and/or prevention of a disease and/or condition caused by the virus. For example, diseases and/or conditions that can be prevented or treated by the disclosed compositions include, but are not limited to, acquired immune deficiency syndrome (AIDS), HBV, HCV, and different forms of malignancies such as leukemia, lymphomas, myelomas, sarcomas, and tumors:

In one embodiment, the disclosed active molecules or pharmaceutical compositions are used to treat or prevent infection and transmission of HIV. In this aspect, a further embodiment of the method includes co-administering an anti-HIV therapy to the subject. An anti-HIV therapy, as used herein, is any therapeutic that is useful for reducing viral load, preventing viral infection, prolonging the asymptotic phase of HIV infection, prolonging the life of a subject infected with HIV, or providing a therapeutic effect to a subject infected with HIV such as treating, inhibiting, preventing, reducing the severity of, or alleviating one or more symptoms associated with HIV. Anti-HIV therapies include, but are not limited to, nucleoside reverse transcriptase inhibitors (NRTIs) such as abacavir, emtricitabine, lamivudine, tenofovir disoproxil fumarate, and zidovudie, non-nucleoside reverse transcriptase inhibitors (NNRTIs) such as efavirenz, etravirine, nevirapine, and rilpivirine; inhibitors of HIV replication, such as protease inhibitors, e.g., atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such as cobicistat, combination HIV medicines such as (i) abacavir and lamivudine, (ii) abacavir, dolutegravir, and lamivudine, (iii) abacavir, lamivudine, and zidovudine, (iv) atazanavir and cobicistat, (v) bictegravir, emtricitabine, and tenofovir alafenamide, (vi) darunavir and cobicistat, (vii) dolutegravir and rilpivirine, (viii) efavirenz, emtricitabine, and tenofovir disoproxil fumarate, (ix) efavirenz, lamivudine, and tenofovir disoproxil fumarate, (x) elvitegravir, cobicistat, emtricitabine, and tenofovir alafenamide fumarate, (xi) elvitegravir, cobicistat, emtricitabine, and tenofovir disoproxil fumarate, (xii) emtricitabine, rilpivirine, and tenofovir alafenamide, (xiii) emtricitabine, rilpivirine, and tenofovir disoproxil fumarate, (xiv) emtricitabine and tenofovir alafenamide, (xv) emtricitabine and tenofovir disoproxil fumarate, (xvi) lamivudine and tenofovir disoproxil fumarate, (xvii) lamivudine and zidovudine, and (xviii) lopinavir and ritonavir; cytokines; and chemokines.

In another embodiment, the disclosed active molecules or pharmaceutical compositions are used to treat or prevent infection and transmission of HBV. In this aspect, a further embodiment of the method includes co-administering an anti-HBV therapy to the subject. An anti-HBV therapy, as used herein, is any therapeutic that is useful for reducing viral load, preventing viral infection, prolonging the life of a subject infected with HBV, or providing a therapeutic effect to a subject infected with HBV such as treating, inhibiting, preventing, reducing the severity of, or alleviating one or more symptoms associated with HBV. Anti-HBV therapies include, but are not limited to, entecavir, lamivudine, adefovir dipivoxil, interferon alpha-2b, pegylated interferon, telbivudine, tenofovir alafenamide, and tenofovir.

The method of treatment and/or prevention includes administering to the subject any one of the disclosed active molecules or pharmaceutical compositions in an amount sufficient to treat or prevent a virus, for example, HIV or HBV. The method will often further include identifying a subject in need of such treatment or prevention. In another embodiment, the method includes delivering the disclosed active molecule or pharmaceutical composition to a site of infection in the subject. Sites of infection of a virus may include, but are not limited to, cervical tissue, blood, oral mucosa, and rectal tissue. In still another embodiment, when the subject is infected or suspected to be infected with HIV, the method may include delivering the active molecule or pharmaceutical composition to an HIV competent host cell of the subject.

If, after the administration of the active molecules or pharmaceutical composition, the subject is still infected with the virus, then an optional step of the method is to continue administration of the active molecules or pharmaceutical composition.

The present disclosure also provides a method of upregulating one or both of A3G and MX2 expression in a subject in need thereof, the method including administering any of the disclosed active molecules or pharmaceutical compositions disclosed above to the subject in a therapeutically effective amount. In some embodiments, the disclosed molecules and compositions result in an increase in expression of one or both of A3G and MX2 by 5%, 10%, 20%, 30%, 40%, 50%, 60%, 70%, 80%, 90%, 95%, or at least any of the foregoing.

In another embodiment, the present disclosure relates to a method for inhibiting replication of any one or more of the viruses disclosed above. In this embodiment, the method includes administering any of the disclosed active molecules or pharmaceutical compositions to the subject in a therapeutically effective amount to inhibit viral replication. For example, the method may include administering any of the disclosed active molecules or pharmaceutical compositions to a subject infected with HIV or HBV in a therapeutically effective amount such that viral replication of the HIV or HBV is inhibited. The disclosed molecules, for example, a glycan strand or oligosaccharide derived from *Streptococcus cristatus* or *Streptococcus mutans*, can act as agents for inhibiting replication of the virus.

In still another embodiment, the present disclosure provides a method of enhancing immune function. The method of enhancing immune function includes administering any of the disclosed active molecules or pharmaceutical compositions to a subject in need thereof in a therapeutically effective amount to enhance immune function.

In yet another embodiment, the present disclosure provides a method of inhibiting viral infection of a cell, for example, a THP-1 cell. The method of inhibiting viral infection includes contacting the cell with any of the disclosed active molecules to inhibit viral entry into the cell. The disclosed molecules, for example, a glycan strand, a disaccharide molecule, or an oligosaccharide derived from *Streptococcus cristatus* or *Streptococcus mutans*, can act as agents for inhibiting viral entry into cells.

The disclosed compositions can be administered to a subject in need thereof in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules that may be administered with the disclosed compositions include, but are not limited to, cytokines, chemotherapeutic agents, radionuclides, other immunotherapeutics, enzymes, antimicrobials, antibiotics, antifungals, antivirals, anti-HIV therapies including, but not limited to, nucleoside reverse transcriptase inhibitors (NRTIs) such as abacavir, emtricitabine, lamivudine, tenofovir disoproxil fumarate, and zidovudie, non-nucleoside reverse transcriptase inhibitors (NNRTIs) such as efavirenz, etravirine, nevirapine, and rilpivirine, inhibitors of HIV replication, such as protease inhibitors, e.g., atazanavir, darunavir, fosamprenavir, ritonavir, saquinavir, and tipranavir, fusion inhibitors such as enfuvirtide, CCR5 antagonists such as maraviroc, integrase inhibitors such as dolutegravir and raltegravir, post-attachment inhibitors such as ibalizumab, pharmacokinetic enhancers such as cobicistat, combination HIV medicines such as (i) abacavir and lamivudine, (ii) abacavir, dolutegravir, and lamivudine, (iii) abacavir, lamivudine, and zidovudine, (iv) atazanavir and cobicistat, (v) bictegravir, emtricitabine, and tenofovir alafenamide, (vi) darunavir and cobicistat, (vii) dolutegravir and rilpivirine, (viii) efavirenz, emtricitabine, and tenofovir disoproxil fumarate, (ix) efavirenz, lamivudine, and tenofovir disoproxil fumarate, (x) elvitegravir, cobicistat, emtricitabine, and tenofovir alafenamide fumarate, (xi) elvitegravir, cobicistat, emtricitabine, and tenofovir disoproxil fumarate, (xii) emtricitabine, rilpivirine, and tenofovir alafenamide, (xiii) emtricitabine, rilpivirine, and tenofovir disoproxil fumarate, (xiv) emtricitabine and tenofovir alafenamide, (xv) emtricitabine and tenofovir disoproxil fumarate, (xvi) lamivudine and tenofovir disoproxil fumarate, (xvii) lamivudine and zidovudine, and (xviii) lopinavir and ritonavir, chemokines, anti-HBV therapies including, but not limited to, entecavir, lamivudine, adefovir dipivoxil, interferon alpha-2b, pegylated interferon, telbivudine, tenofovir alafenamide, and tenofovir, anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper I-cells, and other molecules that deactivate or down-regulate suppressor or regulatory T-cells.

The additional therapeutic agents are selected based on the condition, disorder or disease to be treated. For example, the disclosed compositions can be co-administered with one or more additional agents that function to enhance or promote an immune response.

VI. Examples

Example 1: Isolation of Glycan Strands and Derivatives from S. cristatus CC5A

Isolation of the cell wall components of S. cristatus CC5A was performed by the following protocol (1). The cell wall of S. cristatus CC5A was isolated from the bacteria after boiling in 5 percent sodium dodecyl sulfate (SDS) solution for 30 minutes. This step was followed by glass bead disruption and DNAse and RNase digestion. Then, 1 percent SDS was added, and the sample was incubated for 15 minutes at 80° C.

Figure 2A:
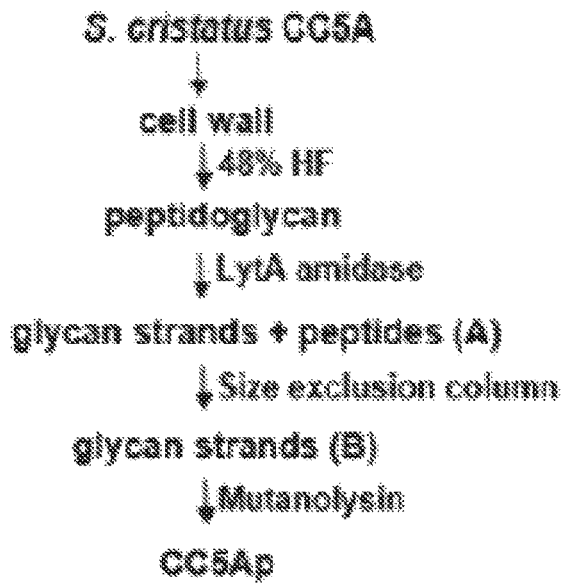
FIG. 2A is a flow chart showing a method for cell wall component isolation.
Figure 2B:
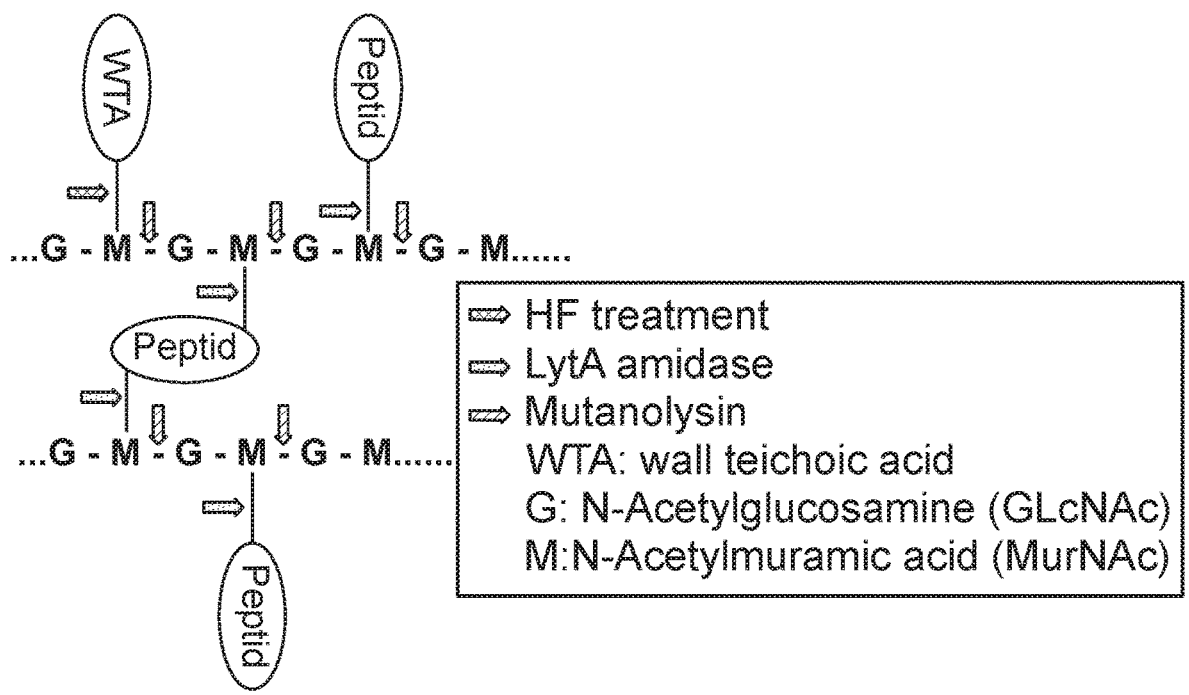
FIG. 2B is a schematic diagram showing cell wall components of bacteria and the cleavage sites for hydrofluoric acid (HF), LytA amidase, and mutanolysin.

The isolated cell wall was subjected to the cell component isolation shown in FIG. 2A. In this process, the wall teichoic acid (WTA) and peptides of the cell wall component were removed by 48 percent hydrofluoric acid (HF) and LytA amidase treatment, respectively, to form glycan strands and peptides (fraction A). Fraction A was purified using a size exclusion column. The remaining glycan strands (fraction B) were cut into GLcNAc-MurNAc (N-Acetyl-D-glucosamine-(1-4)-N-acetylmuramic acid) by mutanolysin treatment. FIG. 2B shows the scheme of cell wall components and the cleavage sites of HF, LytA amidase, and mutanolysin. The final product was a group of small, water-soluble, heat-stable oligosaccharide molecules, termed CC5Ap.

Mass spectrometry analysis data showed that CC5Ap includes three major components (Table 1).

TABLE 1

| CC5Ap Composition | |
| --- | --- |
| m/z | Structure |
| 495.688 | GlcNAc-MurNAc (G-M) |
| 770.281 | MurNAc-GlcNAc-MurNAc (M-G-M) |
| 973.366 | GlcNAc-MurNAc-GlcNAc-MurNAc (G-M-G-M) |

The three components are derivatives of the glycan strands, which build the backbone of the peptidoglycan of S. cristatus CC5A. M-G-M and G-M-G-M are the incomplete digestion products of the glycan strands.

Example 2: CC5Ap Enhances A3G Expression

Materials and Methods

Equal volumes of an S. cristatus CC5A whole cell extract (CC5A1E), fraction A (glycan strands and peptides), fraction B (glycan strands), and CC5Ap were used to treat THP-1 cells for 16 hours. THP-1 cell line is a human monocytic cell line derived from acute monocytic leukemia. The THP-1 cells were obtained from the NIH AIDS Reagent Program. qRT-PCR was used to detect the relative expression of A3G mRNA in THP-1 cells. PBS treated THP-1 cells were used as a control.

In addition, a Live/Dead Cell Vitality Assay Kit (Thermo Fisher Sci, L34951) was used to measure cell viability of THP-1 cells following incubations with PBS, CC5NE, and CC5Ap.

Results

Figure 3A:
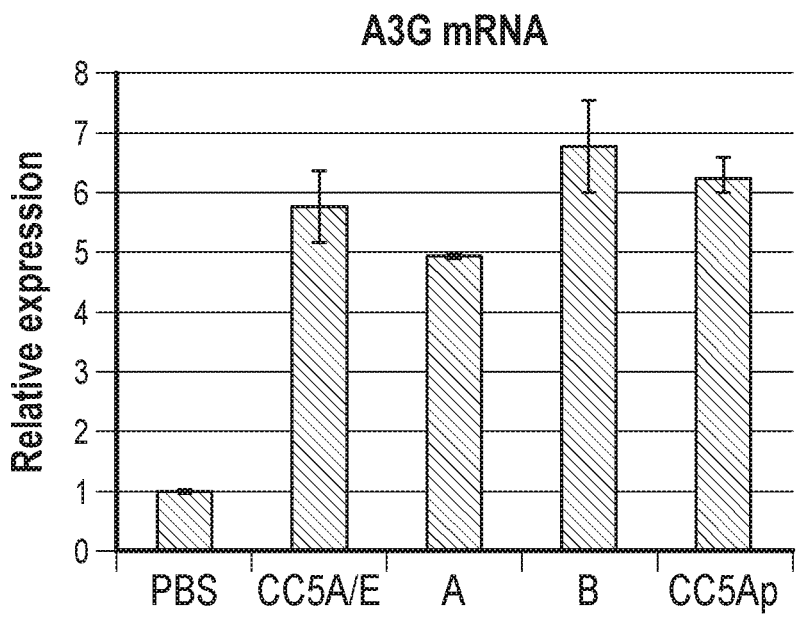
FIGS. 3A and 3B are bar graphs showing that glycan strand and oligosaccharide molecules derived from *Streptococcus cristatus* enhance A3G expression (FIG. 3A) and that glycan strand and oligosaccharide molecules derived from *Streptococcus cristatus* have no observed cytotoxicity (FIG. 3B). Shown are averages±standard deviation of triplicate samples.
Figure 3B:
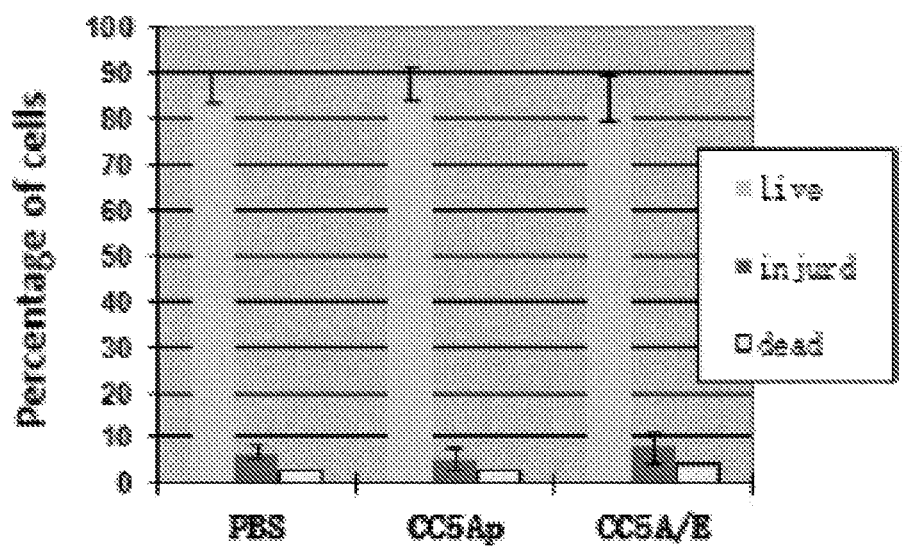

As shown in FIG. 3A, qRT-PCR results demonstrated that both fraction B (soluble glycan strands) and the final product, CC5Ap, induced A3G expression in THP-1 Moreover, as shown in FIG. 3B, CC5Ap and CC5A/E had no observed cytotoxicity to THP-1 cells over a 16 hour period of incubation.

Example 3: Oligosaccharide Fraction of S. Mutans Enhances A3G Expression

Streptococcus Mutans KPSK2 (S. Mu) is a gram-positive bacterium whose cell wall is believed to contain G-M. However, when the cell wall extract of S. Mu was used to treat THP-1 cells, it failed to enhance A3G and A3F expression (2). The purpose of this study was to determine whether oligosaccharide molecules of S. Mu (termed S. Mup) would result in A3G expression.

Materials and Methods

Figure 4:
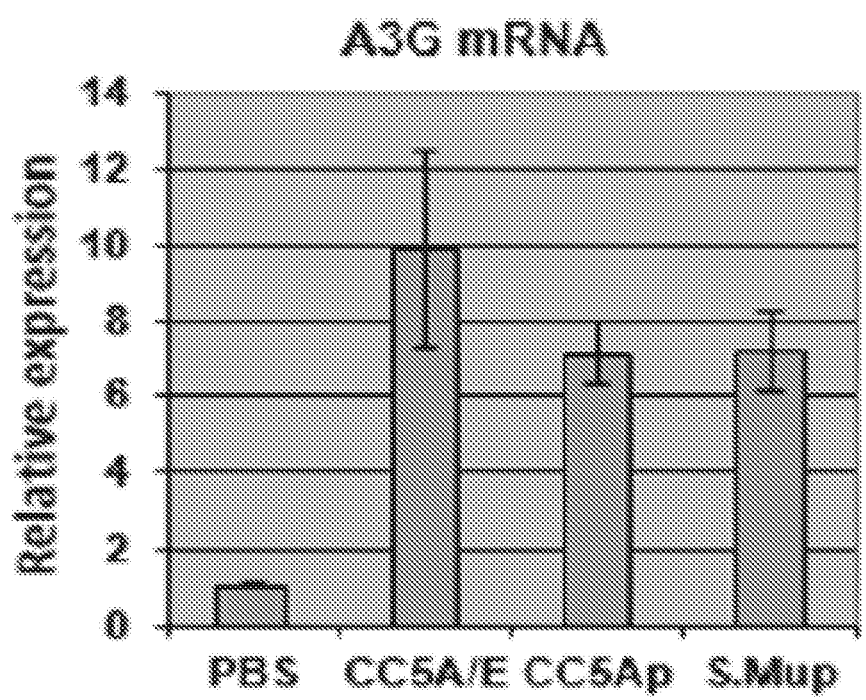
FIG. 4 is a bar graph showing that oligosaccharide molecules derived from *Streptococcus mutans* enhance A3G expression. Shown are averages±standard deviation of triplicate samples.

The cell wall of S. Mu was isolated from the bacteria and the isolated cell wall was subjected to the cell component isolation shown in FIG. 2A. Oligosaccharide molecules (from the same amount of bacteria) of CC5Ap and S. Mu were used to treat THP-1 cells. The THP-1 cells were obtained from the NIH AIDS Reagent Program. PBS and CC5A/E were used as the controls. A3G expression was measured by qRT-PCR.
Results Oligosaccharide molecules of S. Mu enhances A3G expression. As shown in FIG. 4, S. Mup enhanced A3G expression to the same level as CC5Ap. This data further confirms that the oligosaccharide molecules (fragments of the glycan strands) are the active molecules inducing A3G/F expression. The fact that the initial cell wall extract of S. Mu did not induce A3G/F expression may be due to the existence of wall teichoic acid chains or peptide chains which blocked S. Mup induction of A3G.

Example 4: CC5Ap Induces A3G Expression Through TLR2 Mediated Pathway

A3G knockdown and viral cDNA hypermutation assay showed that A3G is involved in the CC5Ap-mediated antiviral effect. The purpose of this study was to determine whether CC5Ap enhances A3G expression through a TLR2 mediated pathway.
Materials and Methods THP-1 cells were transfected by a retroviral vector expressing scramble shRNA, shRNA to TLR2, or shRNA to TLR4, respectively. The THP-1 cells were obtained from the NIH AIDS Reagent Program. After screening and cell cloning, the selected TLR2 and TLR4 knockdown cell lines were subjected to qRT-PCR for detecting TLR mRNA level.

Figure 5A:
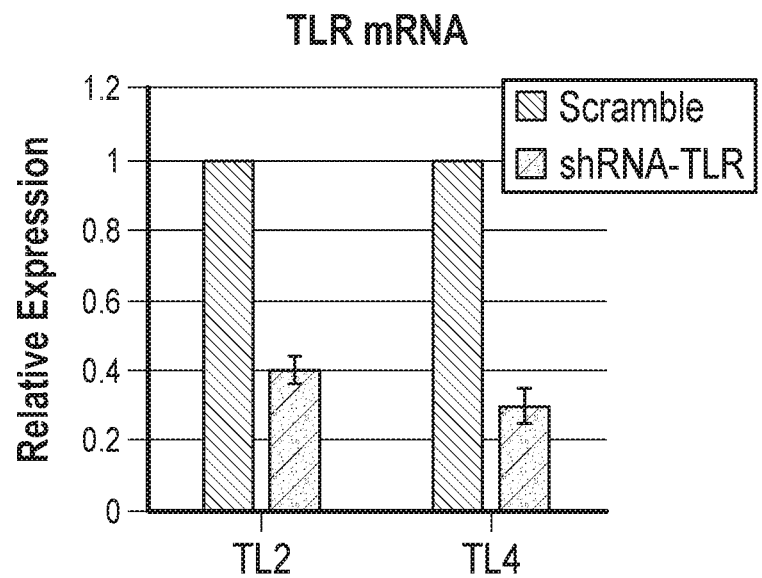
FIGS. 5A and 5B are bar graphs showing that oligosaccharide molecules derived from *Streptococcus cristatus* induce A3G expression through a TLR2 mediated pathway. Shown are averages±standard deviation of triplicate samples.
Figure 5B:
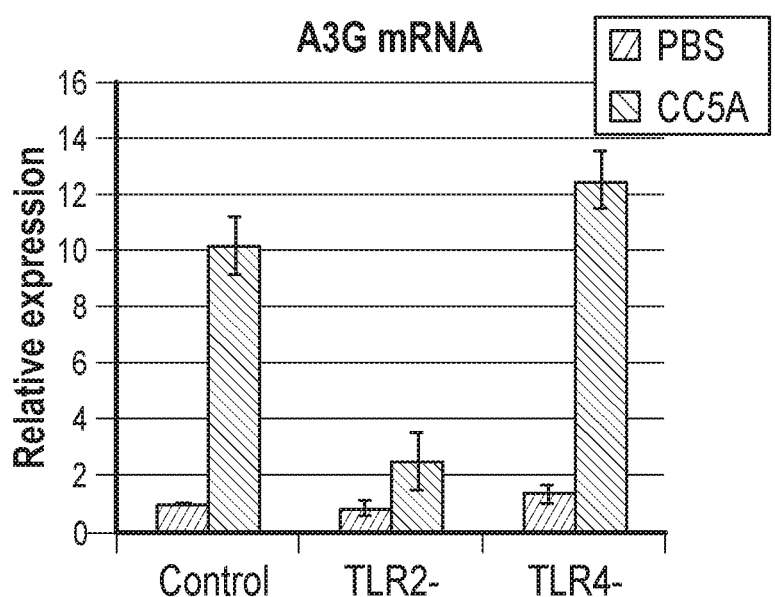

CC5Ap was used to treat THP-1 scramble shRNA, TLR2, and TLR4 knockdown cell lines. A3G expression was measured by qRT-PCR.
Results As shown in FIGS. 5A and 5B, CC5Ap enhanced A3G expression through a TLR2 mediated pathway. This finding is consistent with the data that the TLR2 functional antibody blocked the effect of CC5Ap on inducing A3G expression. However, CC5Ap has no effect on the regulation of A3G expression in CD4+T cells, which lack a TL2 receptor.

Example 5: CC5Ap Induces MX2 Expression and Inhibits Early Stages of HIV Infection MX2 is an interferon-induced, post-entry inhibitor of HIV-1 infection. MX2 specifically targets the early stage of HIV-1 replication, where it inhibits HIV-1 viral integration and renders cells resistant to HIV-1 infection. Although both A3G and MX2 inhibit HIV-1 replication, A3G and MX2 target different stages. MX2 targets the early stages of HIV-1 replication by inhibiting viral cDNA integration. A3G is packaged into new virions and performs its antiviral function upon the second round of infection. The purpose of this study was to determine (1) whether CC5Ap induces MX2 expression and (2) whether CC5Ap plays a role in inhibiting the early stages of HIV-1 replication.
Materials and Methods To determine whether CC5Ap induces MX2 expression, THP-1 cells were treated with different doses (units) of CC5Ap for 16 hours. The THP-1 cells were obtained from the NIH AIDS Reagent Program. One unit of CC5Ap is defined as the amount of CC5Ap needed to induce a 3-fold increase in A3G mRNA expression over a period of 16 hours, using $5 \times 10^5$ THP-1 cells in 500 µl of cell culture medium. MX2 expression was measured by qRT-PCR. After treatment the cells were either subjected to measuring MX2 expression by Western-blot analyses or infected with HIV-1.

To determine whether CC5Ap plays a role in inhibiting the early stages of HIV-1 replication, THP-1 cells were pretreated with CC5Ap or PBS for 48 hours. Cells were washed and infected with HIV-1 IIIB virus (100 ng p24) by 2 hours spinoculation (3). After extensive washing, the cells were cultured for another 24 hours. Culture media were subjected to qRT-PCR to measure viral release.
Results When THP-1 cells were treated with CC5Ap, there was an increase in expression of MX2. As shown in FIGS. 6A and 6B, when THP-1 cells were treated with CC5Ap, there was a dose-dependent increase in the expression of MX2 mRNA (FIG. 6A) and protein (FIG. 6B).

In addition, it was found that CC5Ap inhibits early stages of HIV infection. As shown in FIG. 6C, the viral release from CC5Ap treated cells was significantly lower than that seen in the controls. Because the virus was harvested 24 hours post-infection, the inhibitory effect is less likely due to A3G function as A3G performs its antiviral function in the second round of infection. This indicates that the inhibitory effect is in the early viral replication stage, suggesting CC5Ap inhibits the early stages of HIV-1 replication. These observations suggest that MX2 may mediate the early-stage effects of CC5Ap on HIV-1 replication.

Example 6: CC5Ap Enhances A3G and MX2 Expression and Inhibits HIV-1 Replication in Human Primary Monocyte-Derived Dendritic Cells (DCs)

Figures 7A, 7B:
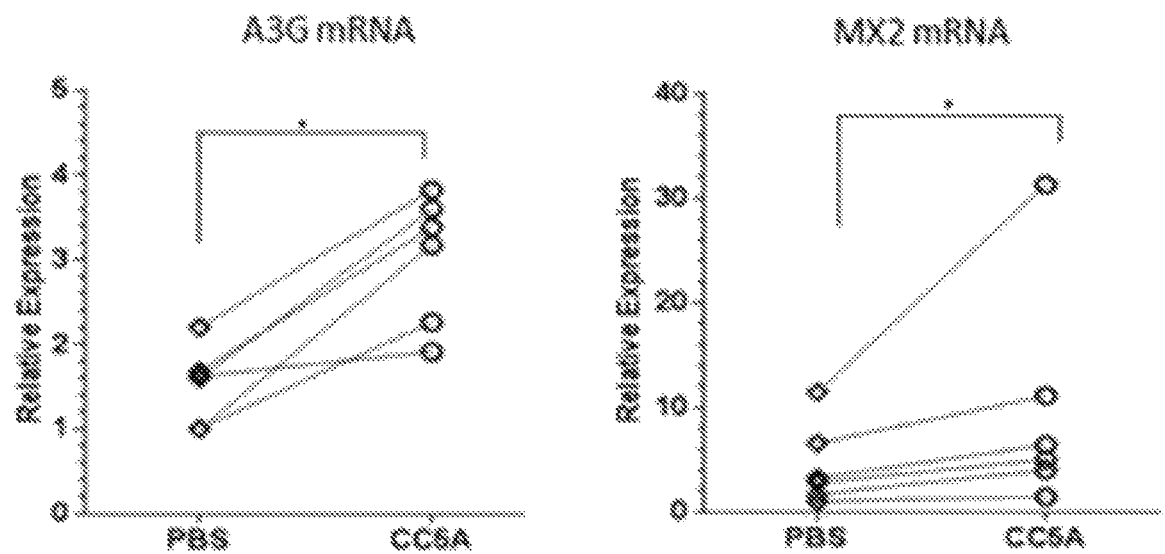
FIGS. 7A, 7B, and 7C are graphs showing that oligosaccharide molecules derived from *Streptococcus cristatus* induces A3G mRNA expression (FIG. 7A) and MX2 mRNA expression (FIG. 7B) and inhibits HIV-1 replication (FIG. 7C) in human primary dendritic cells. Statistical analysis was performed using Wilcoxon t-test.
Figure 7C:
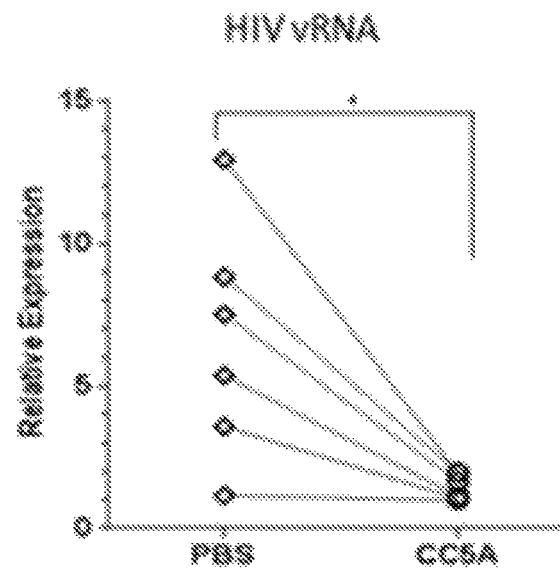

During HIV transmission and early infection, submucosal DCs are among the first targets to encounter the virus (4). DCs are key players in viral transmission, responsible for transmitting HIV to T cells over a period of several days, with transmission dependent on viral replication in the DCs (5). The purpose of this study was to determine whether CC5Ap inhibits HIV replication in DCs.
Materials and Methods Six human monocyte-derived dendritic cell samples (de-identified leukopacks purchased from the New York Blood Center) were treated with PBS or CC5Ap (2 unit) for 16 hours. A3G and MX2 mRNA were measured by qRT-PCR assay. HIV-1 Bal (100 ng p24) was used to infect the treated DCs for 2 hours by spinoculation. After an extensive wash, the DCs were cultured for three days. Viral release was measured by qRT-PCR. Statistical analysis was performed using Wilcoxon t-test.
Results As shown in FIGS. 7A and 7B, CC5Ap significantly increased A3G mRNA levels (FIG. 7A) and MX2 mRNA levels (FIG. 7B). Additionally, as shown in FIG. 7C, CC5Ap inhibited HIV-1 release. A dual effect of CC5Ap on both A3G and MX2 could enhance the ability of CC5Ap to serve as a potent antiviral drug. Even if some viral particles survive MX2 inhibition, A3G will be packaged into the virion and inhibit the second round of HIV-1 infection. By inhibiting HIV replication in DCs, CC5Ap reduces viral transmission from DCs to T cells.

Example 7: GlcNAc-MurNAc (G-M) Enhances A3G and MX2 Expression and Inhibits HIV Replication in THP-1 Cells As shown in Table 1 above, CC5Ap likely contains three oligosaccharide molecules including the sub-unit, G-M. The purpose of this study was to confirm that G-M is an active component in CC5Ap and estimate the G-M concentration of CC5Ap.

Materials and Methods

Synthetic G-M from Toronto Research Chemicals (Cat: A178230) was purchased. The synthetic G-M structure was confirmed by 1H NMR ($D_2O$) and MS. Different doses of G-M were used to treat THP-1 cells. The THP-1 cells were obtained from the NIH AIDS Reagent Program. Specifically, 50 µg, 100 µg, 200 µg and 300 µg/ml G-M (shown in FIGS. 8A-8C as G-M 0.5, 1, 2, 3, respectively) were used to treat THP-1 cells. 1 unit CC5A A/E and CC5Ap were used as the controls. The cells were treated overnight. The mRNA levels of A3G and MX2 were measured by qRT-PCR.

To determine whether G-M inhibits HIV IIIB replication, THP-1 cells were pre-treated 1 hour with G-M or CC5Ap. 100 ng p21 content of IIIB was added into the cell culture to infect the cells overnight. Post-infection, cells were washed 2 times and cultured for nine days. The viral supernatant was subjected to qRT-PCR to measure viral release.

To estimate the G-M concentration, synthetic G-M was used as an external calibration standard to estimate the G-M concentration of CC5Ap using HILIC-MS. Column: Waters Atlantis HILIC; Isocratic Elution: 0.3 mL/min $CH_3CN/H_2O$ (85:15) with $NH_4OAc$/AcOH buffer; Instrument: Thermo-Finnigan TSQ-Quantum UltraMass Spectrometer (Full scan Q1, pos ESI).

Results

Figure 8A:
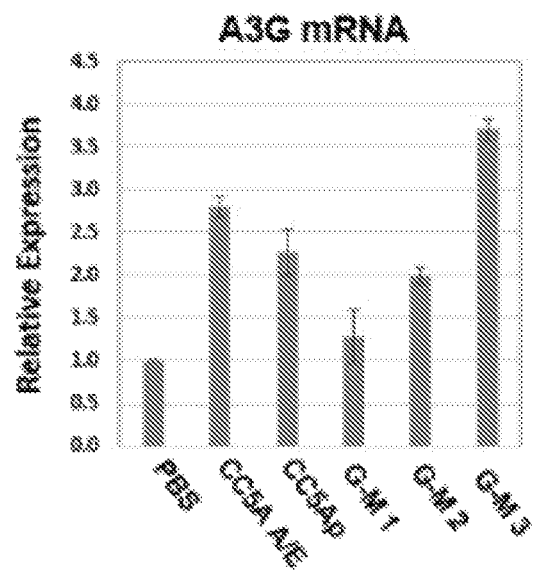
FIGS. 8A and 8B are bar graphs showing that GLcNAc-MurNAc (G-M) enhances A3G mRNA expression (FIG. 8A) and MX2 mRNA expression (FIG. 8B) in THP-1 cells.
Figure 8B:
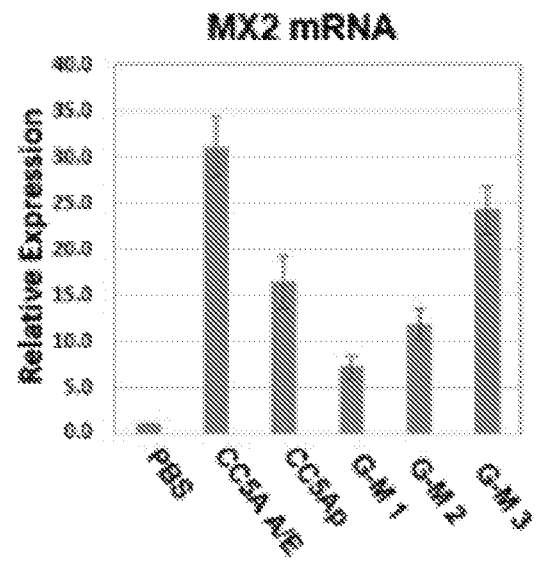
Figure 8C:
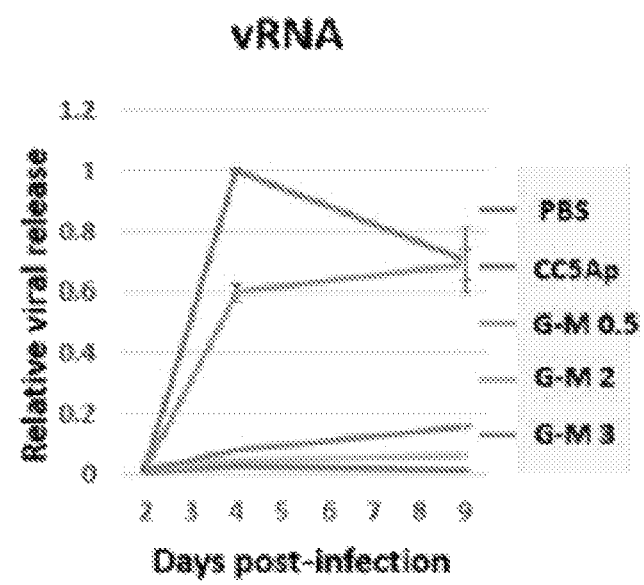
FIG. 8C is a graph showing that G-M inhibits HIV IIIB replication in THP-1 cells. Shown are averages±standard deviation of triplicate samples.

After overnight treatment, G-M enhanced A3G and MX2 mRNA expression. In particular, as shown in FIGS. 8A and 8B, G-M enhanced A3G mRNA expression (FIG. 8A) and MX2 mRNA expression (FIG. 8B) in a dose-dependent manner. Additionally, as shown in FIG. 8C, G-M inhibits HIV IIIB replication in a dose-dependent manner. A noticeable cell number difference between PBS and G-M treated samples was not observed. The data confirms that G-M is one of the active molecules in CC5Ap.

Figure 8D:
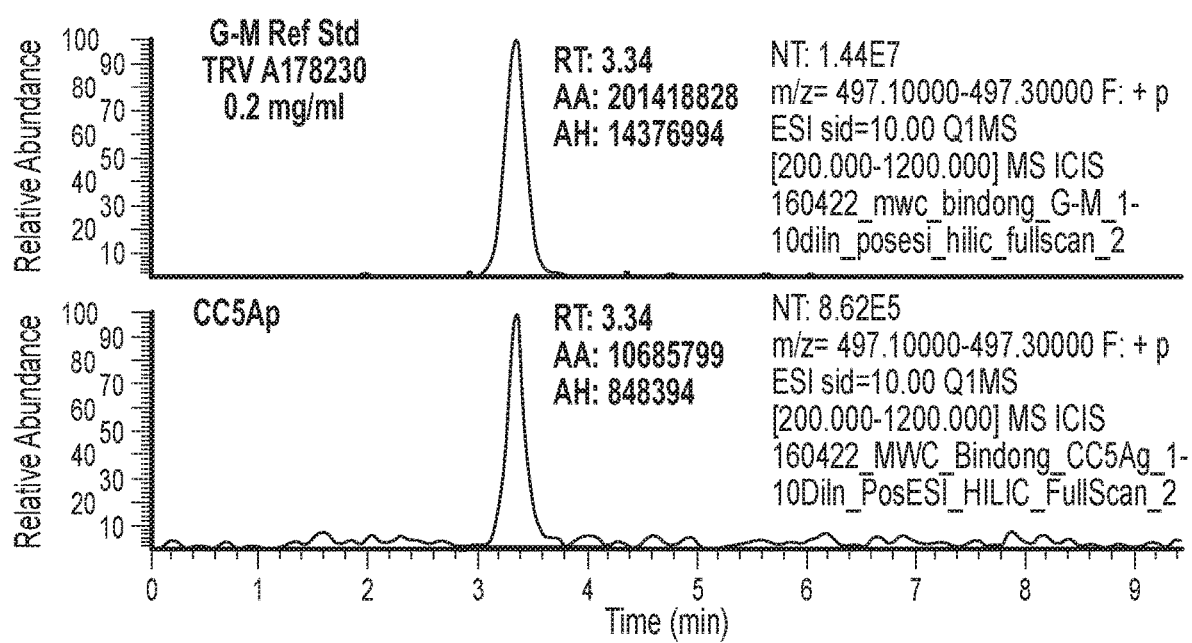
FIG. 8D are graphs from HILIC-MS that were used to estimate the G-M concentration in oligosaccharide molecules derived from *Streptococcus cristatus*.

Using HILIC-MS and the synthetic G-M as an instrument calibration standard, it was estimated that the G-M concentration of the CC5Ap prep was about 100 µg/mL (FIG. 8D). For this prep, 1 unit CC5Ap equals 100 µl. Based on this concentration and the experimentally determined activity of synthetic G-M (0.005 units/µg, FIGS. 8A-8B), G-M accounts for only about 5 percent of the total CC5Ap activity. Therefore, G-M is not the major contributor to CC5Ap activity. As noted in Table 1, CC5Ap comprises G-M, M-G-M and G-M-G-M. Looking at the structure, G-M is part of M-G-M and G-M-G-M. It is possible that the structure of G-M only meets the partial requirement for trigging the enhancement of A3G/MX2 expression. Other chemical groups might be needed to increase the induction.

Example 8: CC5Ap Blocks HIV-1 Transmission in an OKF6/H9 Co-Culture System

Previous data showed that the extract of *S. cristatus* CC5A enhanced A3G expression in VK2/E6E7 (a human vaginal epithelial cell line) and OKF6/TERT-2 cells (OKF6; immortalized human keratinocytes) (2). The purpose of this study was to test whether CC5Ap had an effect on inhibiting HIV-1 transmission in OKF6 cells.

Materials and Methods

The followings doses of CC5Ap, 0, 0.12, 0.25, and 0.5 units, were used to treat OKF6 cells for 72 hours. The OKF6 cells were obtained from Dr. James Rheinwald at Harvard institutes of Medicine. After treatment, HIV-1 IIIB (100 ng p24) was used to inoculate OKF6 cells. After 0.05% trypsin digestion at room temperature and an extensive wash, H9 cells (human CD4+ T cell line) were added into the culture and cultured for 7 days. Supernatant samples were collected for measuring viral release by an HIV-1 p24 ELISA.

Results

Figure 9:
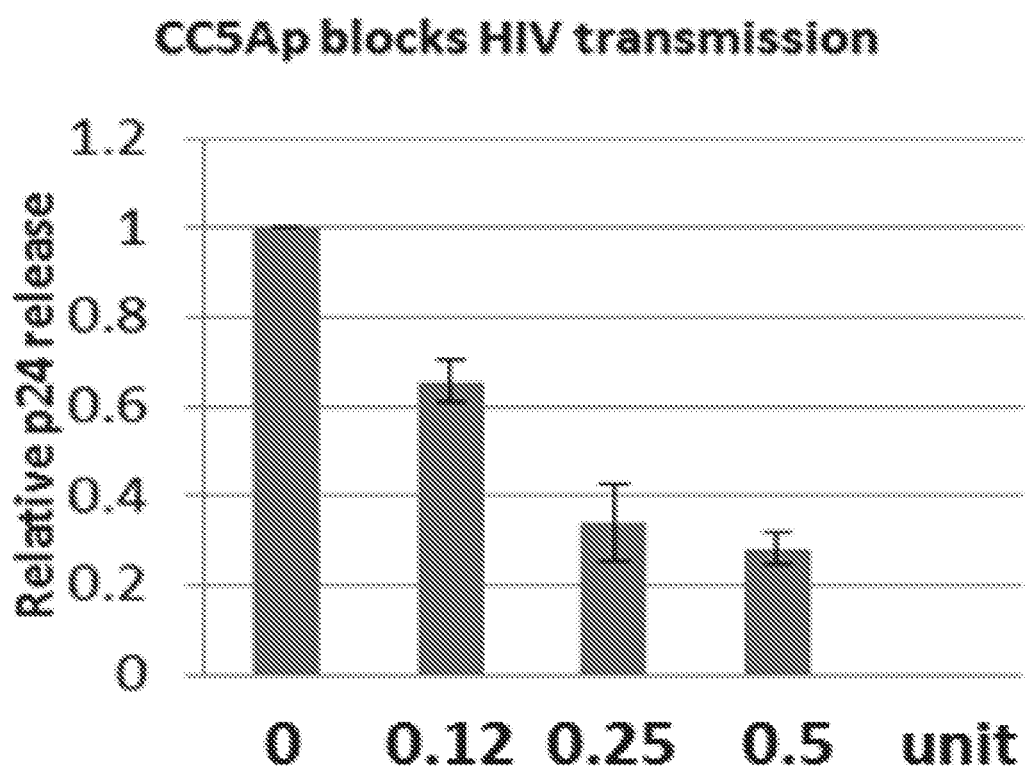
FIG. 9 is a bar graph showing that oligosaccharide molecules derived from *Streptococcus cristatus* block HIV-1 transmission in an OKF6/H-19 co-culture system. Shown are averages±standard deviation of triplicate samples.

As shown in FIG. 9, in the OKF6/TERT-2 and H9 co-culture system, the viral release gradually decreased following the addition of increasing amounts of CC5Ap, indicating CC5Ap inhibits HIV-1 transmission from OKF6 to H9 cells. Since H9 cells were added into the system after CC5Ap had been removed by the wash step, the reduction of p24 release was unlikely due to the effect of CC5Ap on H9 cells.

Example 9: CC5Ap Inhibits Founder/Transmitted HIV Replication in a Human Cervical Explant Assay Materials and Methods De-identified human cervical epithelial tissues were acquired through the Cooperative Human Tissue Network at Vanderbilt. Dermal biopsy punches (3 mm) were used to cut full-thickness tissue specimen. Six punch pieces were obtained from donor 1 and nine punch pieces were obtained from donor 2. The punches from each donor were divided into three groups. Each group was treated with PBS, 0.5 unit, and 1 unit of CC5Ap for 1 hr. Then 100 ng of the p24 content of founder/transmitted virus SUMA0874 was used to infect the tissues overnight. Afterward, the epithelium tissues were washed 5 times. The infected tissues were cultured in fresh medium for four days. The culture supernatant was harvested and subjected to qRT-PCR to measure viral genome RNA.

Results

Figure 10:
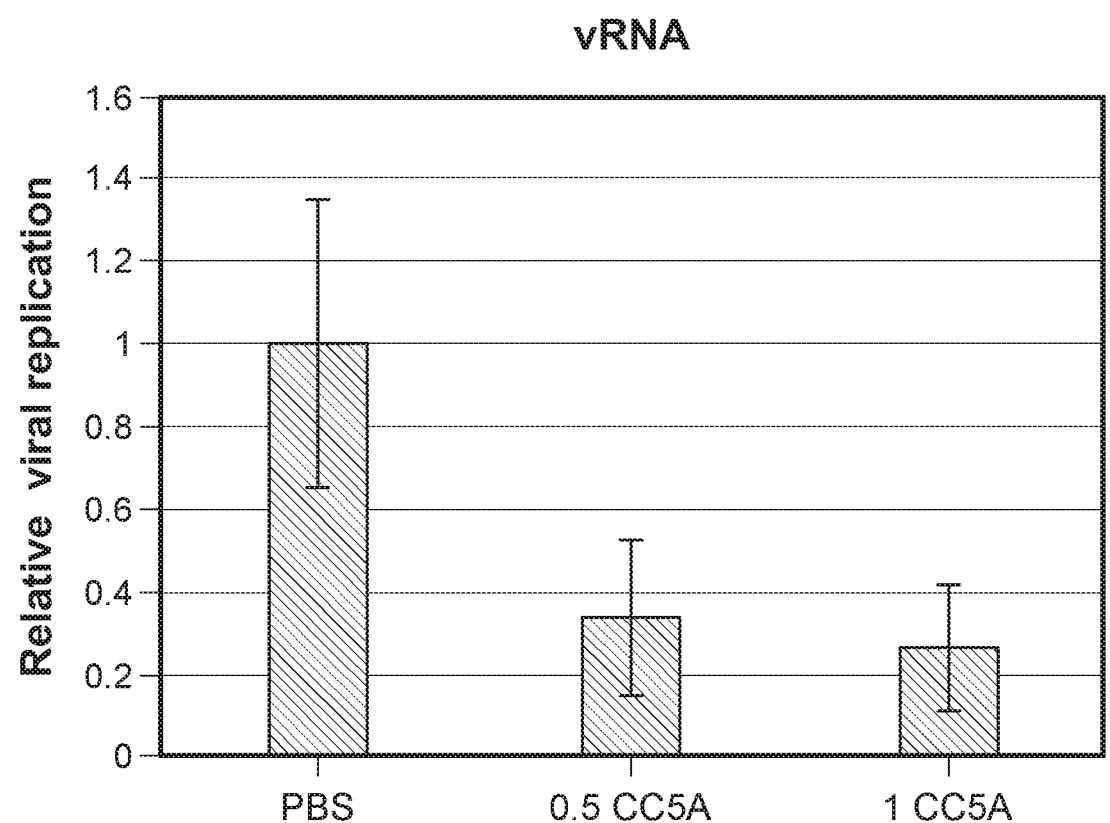
FIG. 10 is a bar graph showing that oligosaccharide molecules derived from *Streptococcus cristatus* inhibit HIV founder/transmitted virus replication in a human cervical explant assay. Shown are averages±standard deviation of 5 samples.
Figure 11A:
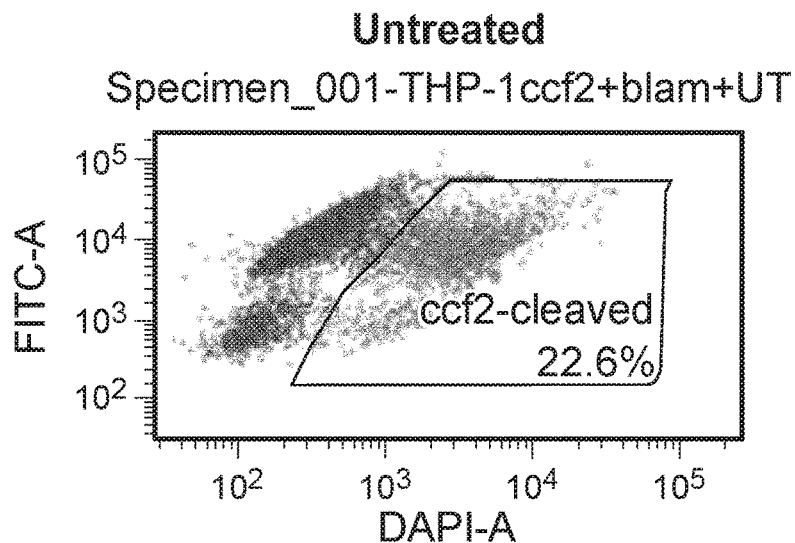
FIGS. 11A-11F are graphs showing viral entry of THP-1 cells treated with various amounts of the untreated control, the HIV entry inhibitor (AMD3100), CC5A/PBS, and the disaccharide molecule, G-M, after analysis by FACSAria III for CCF2 (green/FITC-A) and cleaved CCF2 (DAPI-A) florescence.
Figure 11B:
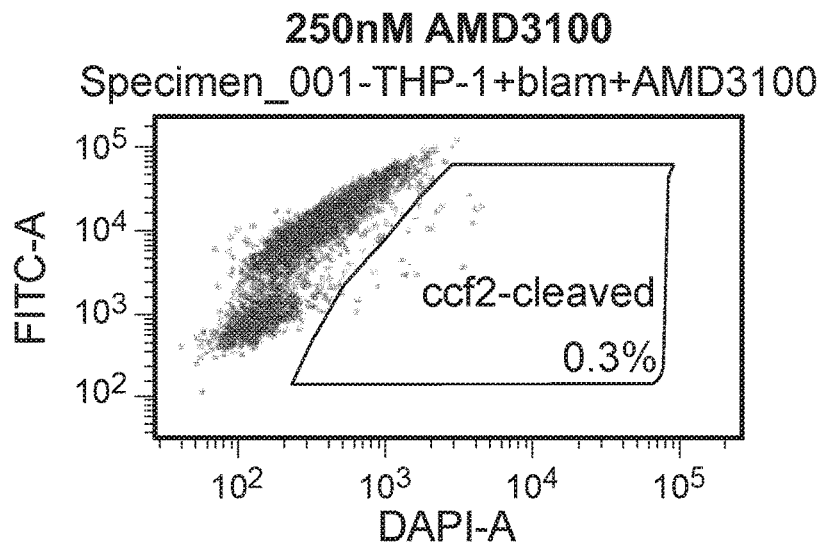
Figure 11C:
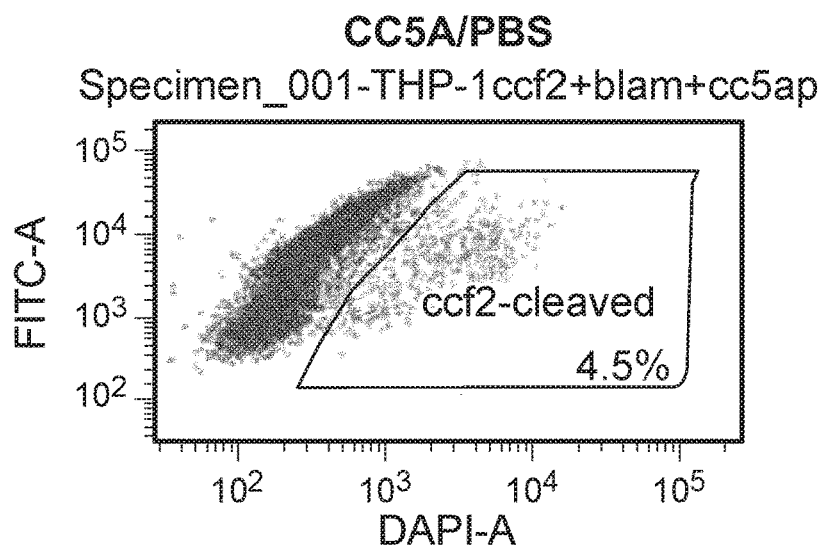
Figure 11D:
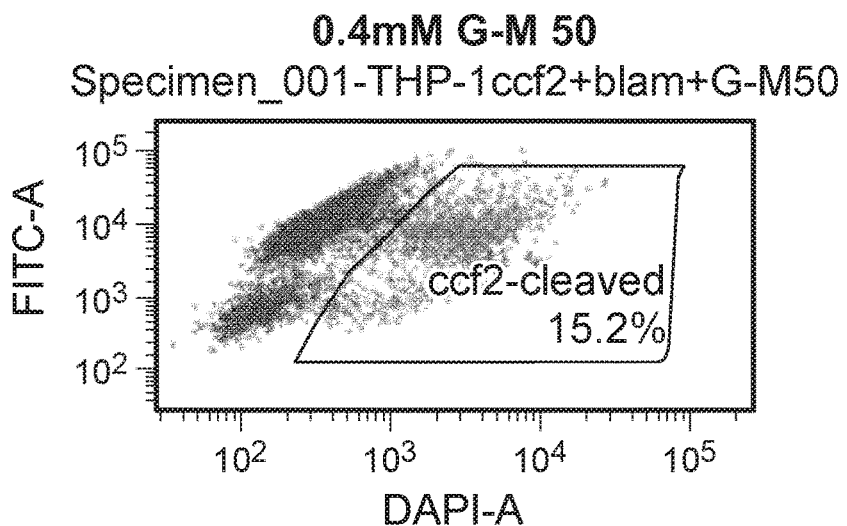
Figure 11E:
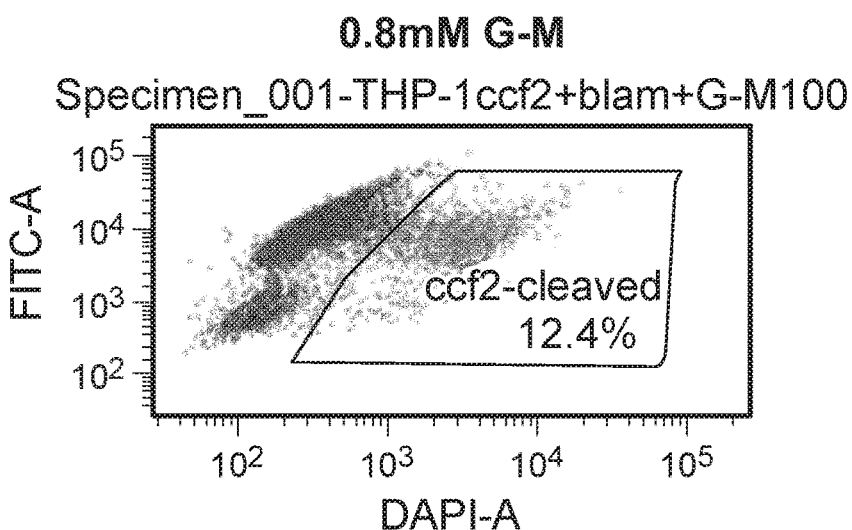
Figure 11F:
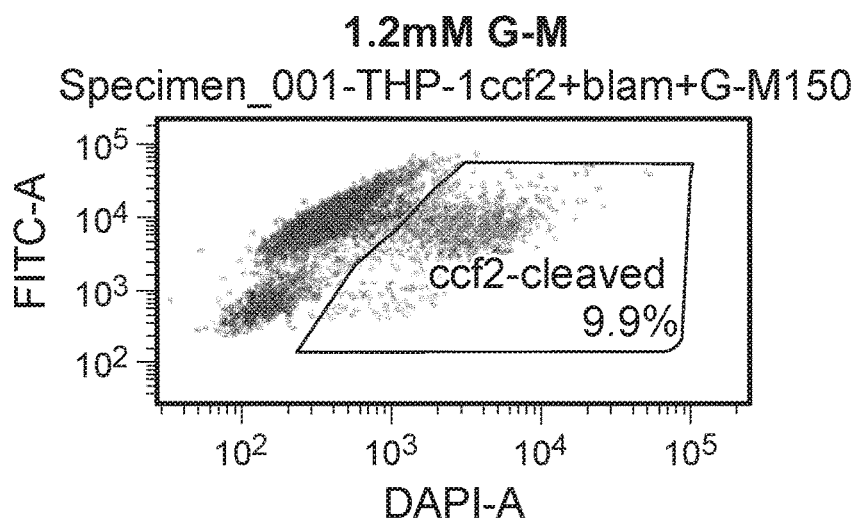

As shown in FIG. 10, CC5Ap dramatically inhibited SUMA0874 replication in a dose-dependent manner. The data suggests that CC5Ap is a promising anti-HIV drug candidate.

Example 10: CC5A/PBS and G-M Inhibit HIV-1 Viral Entry

CC5A/PBS Preparation

After washing *S. Cristatus* CC5A cells with PBS three times, the cells were incubated in PBS buffer at 37° C. for three hours. The solution (termed as CC5A/PBS) was collected after the cells were removed by high-speed centrifugation.

Materials and Methods

To determine whether the disclosed molecules have effects on HIV-1 viral entry, a sensitive and specific enzyme-based assay developed by Marielle et al (6) was used. THP-1 cells were pre-treated with AMD3100 (HIV entry inhibitor), CC5A/PBS (cell lysate of *Streptococcus Cristatus* CC5A), and different amounts of G-M (GlcNAc-MurNAc, which is a disaccharide molecule of glycan strain) overnight. PBS treated THP-1 cells were used as the untreated control. After washing, Vpr-BlaM containing HIV NL4-3 virus was used to infect the cells. After washing again, the cells were subjected to CCF2 staining overnight. The following day, the cells were analyzed by FACSAria III for CCF2 (green/FITC-A) and cleaved CCF2 (DAPI-A) florescence.

Results

FIGS. 11A-11F are graphs showing viral entry of THP-1 cells treated with various amounts of the untreated control, the HIV entry inhibitor (AMD3100), CC5/PBS, and the disaccharide molecule, G-M, after analysis by FACSAria III for CCF2 (green/FITC-A) and cleaved CCF2 (DAPI-A) florescence. Increased viral entry is displayed as more cleaved CCF2 (DAPI-A).

Figure 12:
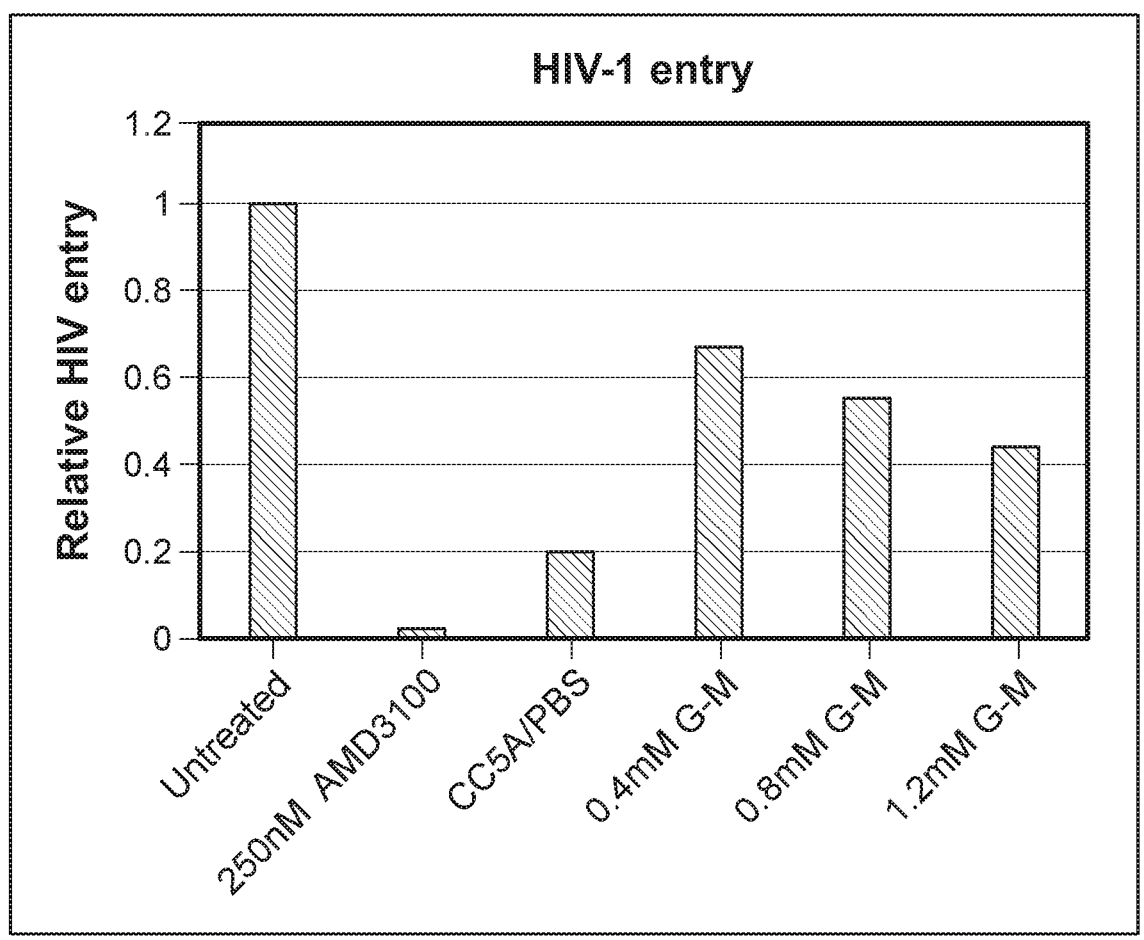
FIG. 12 is a bar graph showing that THP-1 cells treated with the disclosed molecules, including CC5A/PBS and varying amounts of G-M, inhibit HIV-1 viral entry when compared to the untreated control.
Figure 13A:
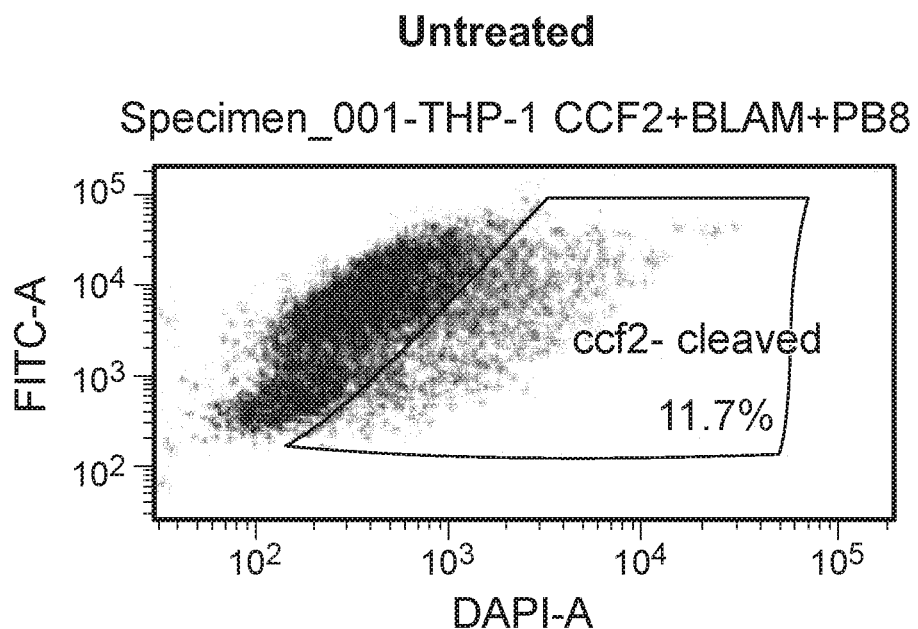
FIGS. 13A-13E are graphs showing viral entry of THP-1 cells treated with various amounts of the untreated control, the HIV entry inhibitor (AMD3100), CC5A/PBS, CC5Ap, and S.MuP after analysis by FACSAria III for CCF2 (green/FITC-A) and cleaved CCF2 (DAPI-A) florescence.
Figure 13B:
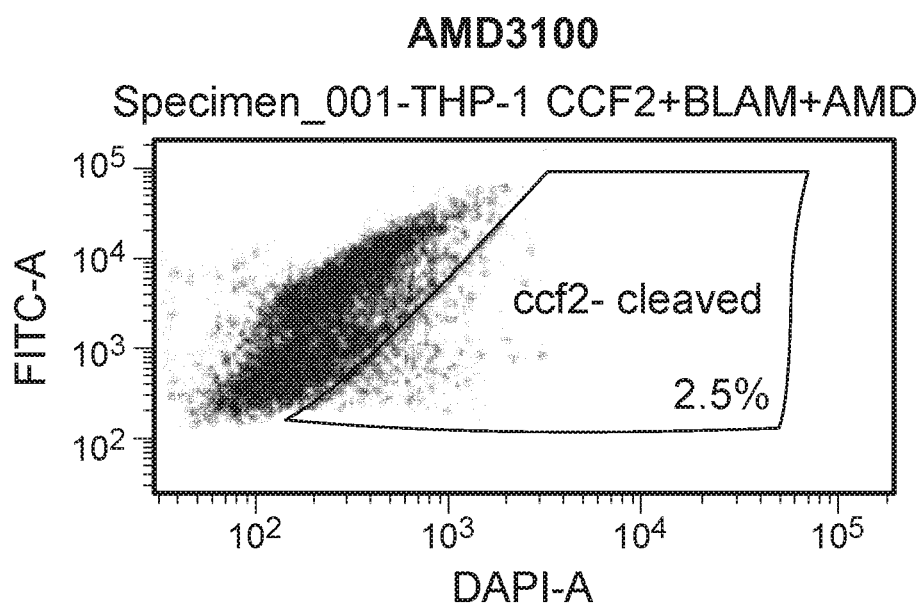
Figure 13C:
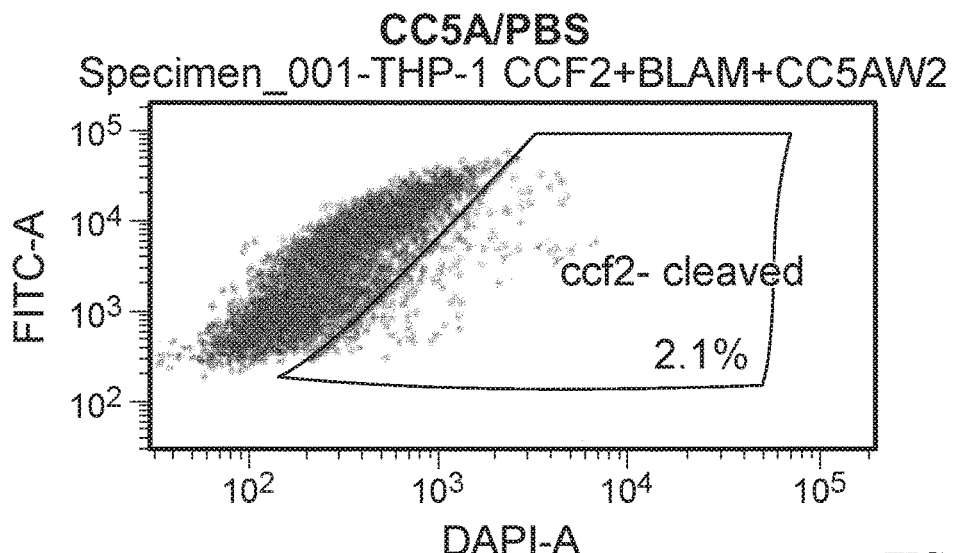
Figure 13D:
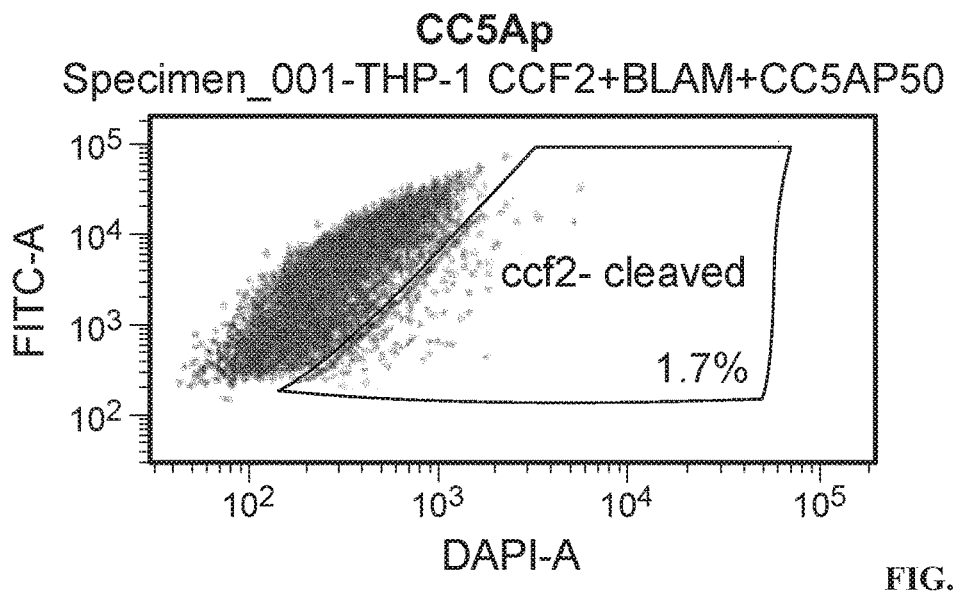
Figure 13E:
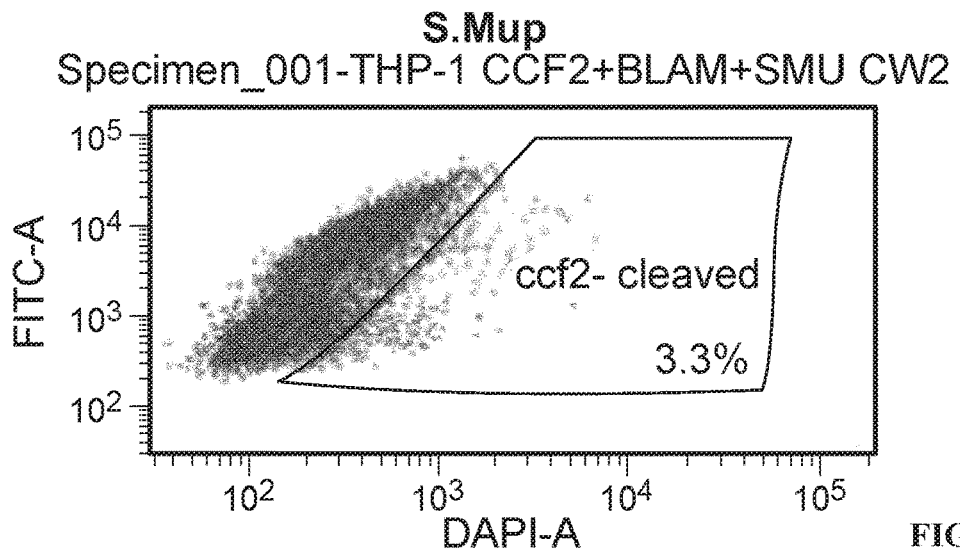

FIG. 12 is a bar graph representing the quantitative results of FIGS. 11A-11F. More specifically, FIG. 12 shows the relative HIV entry of THP-1 cells treated with the HIV entry inhibitor (AMD3100), CC5A/PBS, and various amounts of G-M. As shown in FIG. 12, THP-1 cells treated with CC5A/PBS or the disaccharide molecule (G-M) reduced HIV entry dramatically when compared to the untreated control.

Example 11: CC5Ap and S. MuP Inhibits HIV-1 Viral Entry

Materials and Methods

THP-1 cells were treated with CC5Ap and with cell lysate from *Streptococcus Mutant* (S. MuP). The protocol described in Example 10 was followed to test the effects of CC5Ap and S.MuP on HIV viral entry.

Results

FIGS. 13A-13E are graphs showing viral entry of THP-1 cells treated with various amounts of the untreated control, the HIV entry inhibitor (AMD3100), CC5A/PBS, CC5Ap, and S.MuP after analysis by FACSAria III for CCF2 (green/FITC-A) and cleaved CCF2 (DAPI-A) florescence. Increased viral entry is displayed as more cleaved CCF2 (DAPI-A).

Figure 14:
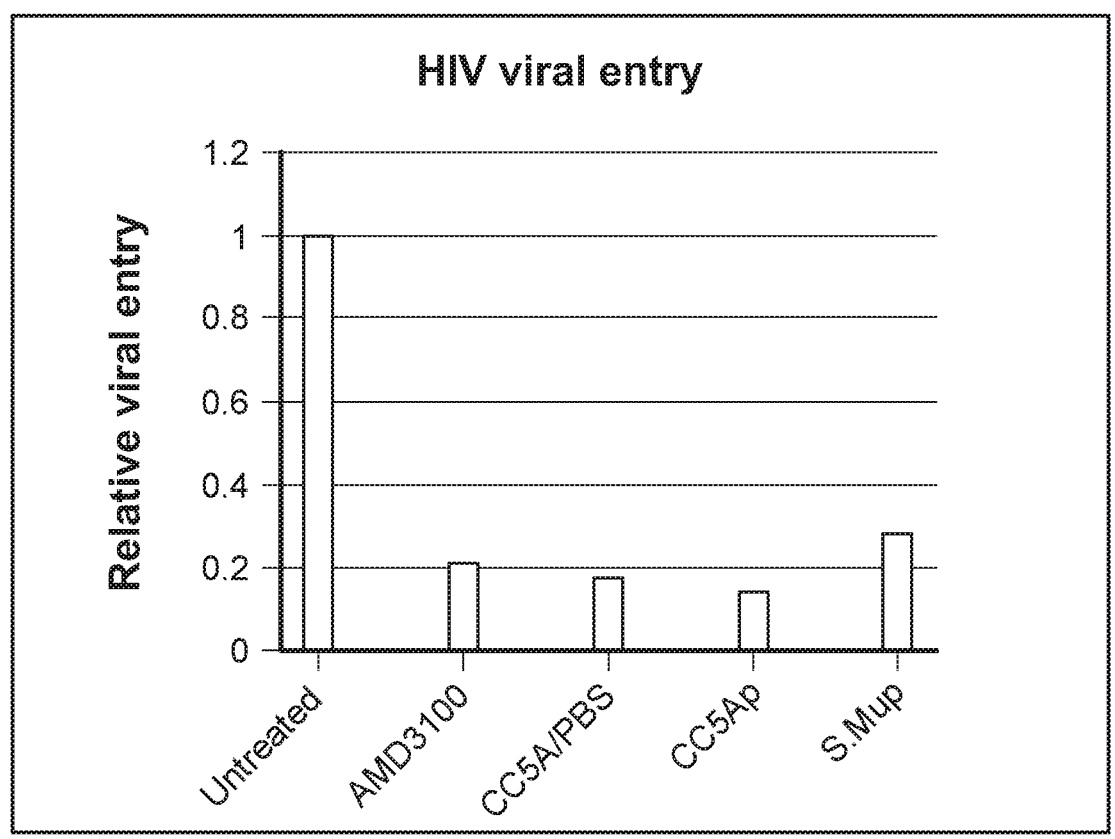
FIG. 14 is a bar graph showing that THP-1 cells treated with CC5Ap and *Streptococcus Mutant* (S. Mup) inhibit HIV-1 viral entry when compared to the untreated control.

FIG. 14 is a bar graph representing the quantitative results of FIGS. 13A-13E. That is, FIG. 14 shows the relative HIV entry of THP-1 cells treated with the HIV entry inhibitor (AMD3100), CC5A/PBS, CC5Ap, and S.MuP. As shown in FIG. 14, THP-1 cells treated with CC5Ap and S.MuP dramatically inhibited HIV entry into THP-1 cells.

Example 12: CC5A/PBS has No Effects on CD4 and CXCR4 Expression

Materials and Methods

Since it was demonstrated that CC5A/PBS treatment inhibits HIV entry in the THP-1 cell line (as described in Example 10), testing was performed to determine whether CC5A/PBS has effects on CD4 and CXCR4 expression. The expression of CD4 and CXCR4 on the surface of the THP-1 cells were measured by FACSCalibur.

Results

Figure 15A:
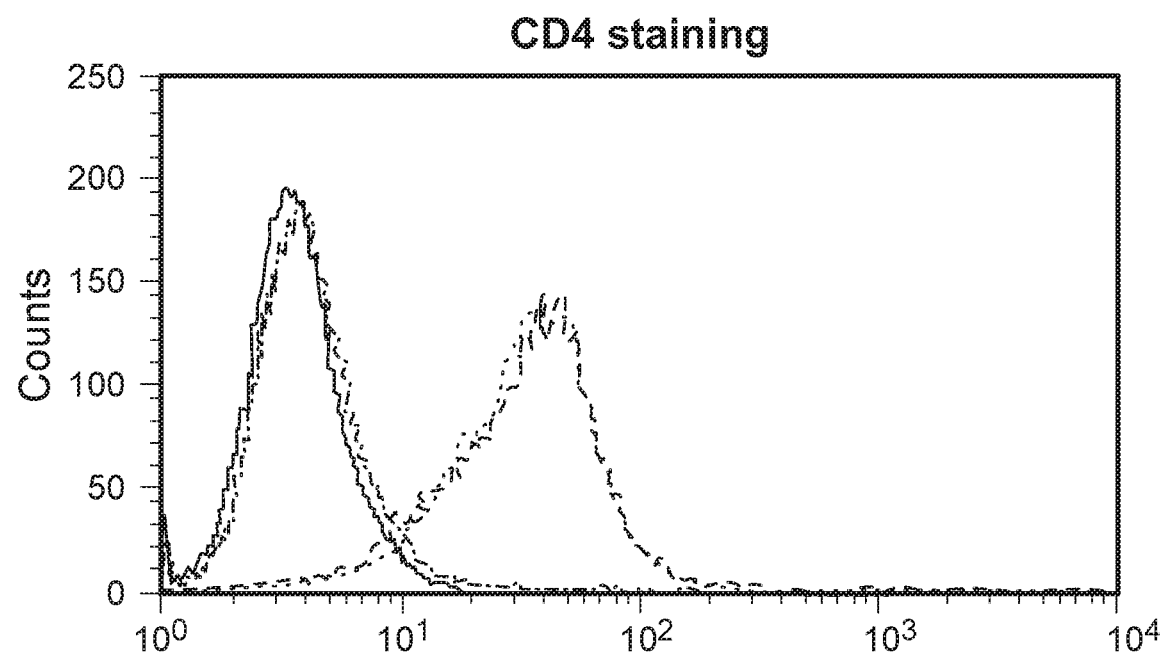
FIG. 15A is a graph showing that the treatment of CC5A/PBS has no effects on CD4 expression.
Figure 15B:
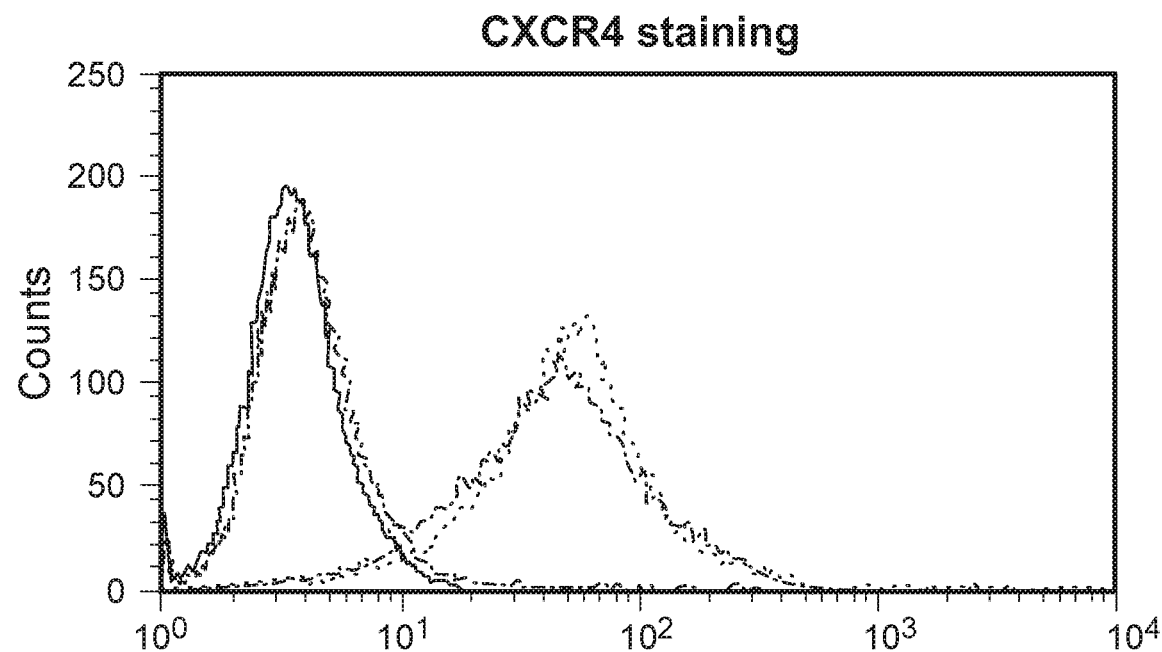
FIG. 15B is a graph showing that the treatment of CC5A/PBS has no effects on CXCR4 expression.

FIG. 15A shows a graph of the CD4 staining while FIG. 15B shows a graph of the CXCR4 staining. As shown in FIGS. 15A and 15B, the treatment of CC5A/PBS had no effects on CD4 and CXCR4 expression.

REFERENCES

1. Bui N K, Eberhardt A, Vollmer D, Kern Bougault C, Tomasz A, Simorre J P, Vollmer W. 2012. Isolation and analysis of cell wall components from *Streptococcus pneumoniae, Anal Biochem* 421:657-666.
2. Wang Z, Luo Y, Shao Q, Kinlock B L, Wang C, Hildreth J E Xie H, Liu B. 2014. Heat-stable molecule derived from *Streptococcus cristatus* induces APOBEC3 expression and inhibits HIV-1 replication. *PLoS One* 9: e106078.
3. O'Doherty U, Swiggard W J, Malim M H. 2000. Human immunodeficiency virus type 1 spinoculation enhances infection through virus binding. *J Virol* 74:10074-10080.
4. Wu L, KewalRamani V N. 2006. Dendritic-cell interactions with HIV: infection and viral dissemination. *Nat Rev Immunol* 6:859-868.
5. Coleman C M, Wu L. 2009. HIV interactions with monocytes and dendritic cells: viral latency and reservoirs, *Retrovirology* 6:51.
6. Marielle et al. November 2002. *Nature Biotech* 1151-1154.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method of treating one or both of HIV and HBV in a subject in need thereof, comprising: administering to the subject an effective amount of a pharmaceutical composition comprising a pharmaceutically acceptable carrier and a glycan strand comprising GlcNAc-MurNAc (G-M), MurNAc-GlcNAc-MurNAc (M-G-M), and GlcNAc-MurNAc-GlcNAc-MurNAc (G-M-G-M).

2. A method of upregulating one or both of A3G and MX2 in a subject in need thereof, comprising: administering to the subject an effective amount of a pharmaceutical composition comprising a pharmaceutically acceptable carrier and a glycan strand comprising GlcNAc-MurNAc (G-M), MurNAc-GlcNAc-MurNAc (M-G-M), and GlcNAc-MurNAc-GlcNAc-MurNAc (G-M-G-M).

3. A method of reducing replication of one or both of HIV and HBV in a cell, comprising: contacting the cell with an effective amount of a glycan strand comprising GlcNAc-MurNAc (G-M), MurNAc-GlcNAc-MurNAc (M-G-M), and GlcNAc-MurNAc-GlcNAc-MurNAc (G-M-G-M).

4. A method of reducing one or both of HIV and HBV infection of a cell, comprising: contacting the cell with an effective amount of a glycan strand comprising GlcNAc-MurNAc (G-M), MurNAc-GlcNAc-MurNAc (M-G-M), and GlcNAc-MurNAc-GlcNAc-MurNAc (G-M-G-M).

5. The method of claim 1, wherein the glycan strand is water-soluble and heat stable.

6. The method of claim 1, wherein the pharmaceutical composition is formulated for parenteral administration.

7. The method of claim 1, wherein the pharmaceutical composition is formulated for transmucosal administration.

8. The method of claim 2, wherein the pharmaceutical composition is formulated for parenteral administration selected from intramuscular, intraperitoneal, intravenous, or subcutaneous administration.

9. The method of claim 2, wherein the pharmaceutical composition is formulated for at least one of: oral delivery, vaginal delivery, and rectal delivery.

10. The method of claim 2, wherein the pharmaceutical composition is formulated for topical delivery.

11. The method of claim 3, wherein the glycan strand is water-soluble and heat stable.

12. The method of claim 4, wherein the glycan strand is water-soluble and heat stable.

13. The method of claim 3, wherein the cell is a THP-1 cell.

14. The method of claim 4, wherein the cell is a THP-1 cell.

15. The method of claim 3, wherein the glycan strand has a molecular weight of greater than about 450 Da.

16. The method of claim 4, wherein the glycan strand has a molecular weight of greater than about 750 Da.

\* \* \* \* \*